(12) United States Patent
Abdou

(10) Patent No.: US 7,331,961 B2
(45) Date of Patent: *Feb. 19, 2008

(54) PLATING SYSTEM FOR BONE FIXATION AND SUBSIDENCE AND METHOD OF IMPLANTATION

(76) Inventor: M. Samy Abdou, 7790 Doug Hill, San Diego, CA (US) 92127

( * ) Notice: Subject to any disclaimer, the term of this patent is extended or adjusted under 35 U.S.C. 154(b) by 3 days.

This patent is subject to a terminal disclaimer.

(21) Appl. No.: 10/755,080

(22) Filed: Jan. 10, 2004

(65) Prior Publication Data

US 2004/0204713 A1 Oct. 14, 2004

Related U.S. Application Data

(63) Continuation-in-part of application No. 10/683,325, filed on Oct. 10, 2003.

(60) Provisional application No. 60/439,030, filed on Jan. 10, 2003.

(51) Int. Cl.
*A61B 17/56* (2006.01)

(52) U.S. Cl. ........................................ 606/71

(58) Field of Classification Search ............ 606/61, 606/69, 70, 71, 72, 73
See application file for complete search history.

(56) References Cited

U.S. PATENT DOCUMENTS

| | | |
|---|---|---|
| 5,487,742 A | 1/1996 | Cotrel |
| 5,616,142 A | 4/1997 | Yuan |
| 5,681,311 A | 10/1997 | Foley |
| 5,681,313 A | 10/1997 | Diez |
| 5,704,936 A | 1/1998 | Mazel |
| 5,707,372 A | 1/1998 | Errico et al. |

(Continued)

OTHER PUBLICATIONS

The Effect of Cutting Flute Design on the Insertion and Pullout Properties of Self-tapping Bone Screws; Scott Yerby, Ph.D., C. Corey Scott, MS, Nathan J. Evans, MS, Katie L. Messing, MS, and Dennis R. Carter, Ph.D.; pp. 1-2; Jul. 2, 2002.

(Continued)

*Primary Examiner*—Eduardo C. Robert
*Assistant Examiner*—Michael J. Araj
(74) *Attorney, Agent, or Firm*—Fish & Richardson P.C.; Fred C. Hernandez

(57) ABSTRACT

A bone plating system is provided that permits maintenance of a compression force while also accommodating bony subsidence, among other features. Methods of implantation are also provided that improve alignment and placement during implantation and avoid maneuvers that weaken the vertebral bodies. A modular distraction screw is placed during the initial stages of surgery when all relevant landmarks are still intact. After completion of the surgical bone work, a proximal end of the distraction screw is detached, leaving a protruding distal segment implanted in the centerline of the vertebral bodies above and below the newly fused disc space. A bone plate is guided into proper position relative to the upper and lower vertebra by attaching the bone plate to the protruding distal segments. The distal segments of the distraction screws are tightened onto the plate and the plate is held stationary while bone screws are placed. The bone plating system is also extendable, allowing additional bone plates to be placed and coupled with existing plate components to create a multi-level plating system. Additional bone plates may be placed contemporaneously or during a subsequent surgical procedure.

18 Claims, 21 Drawing Sheets

U.S. PATENT DOCUMENTS

| | | |
|---|---|---|
| 5,709,686 A | 1/1998 | Talos et al. |
| 5,713,900 A | 2/1998 | Benzel et al. |
| 5,716,357 A | 2/1998 | Rogozinski |
| 5,735,853 A | 4/1998 | Olerud |
| 5,904,683 A | 5/1999 | Pohndorf et al. |
| 5,954,722 A | 9/1999 | Bono |
| 5,964,763 A | 10/1999 | Incavo et al. |
| 6,139,316 A | 10/2000 | Sachdeva et al. |
| 6,306,136 B1 | 10/2001 | Baccelli |
| 6,331,179 B1 | 12/2001 | Freid et al. |
| 6,402,756 B1 | 6/2002 | Ralph et al. |
| 2002/0183755 A1 | 12/2002 | Michelson |

OTHER PUBLICATIONS

Day Surgery for Anterior Cervical Microdiskectomy: Experience with 75 Cases, Richard N.W. Wohns, M.D. and Roger D. Robinett, M.D., pp. 1-3, Jul. 11, 2002.

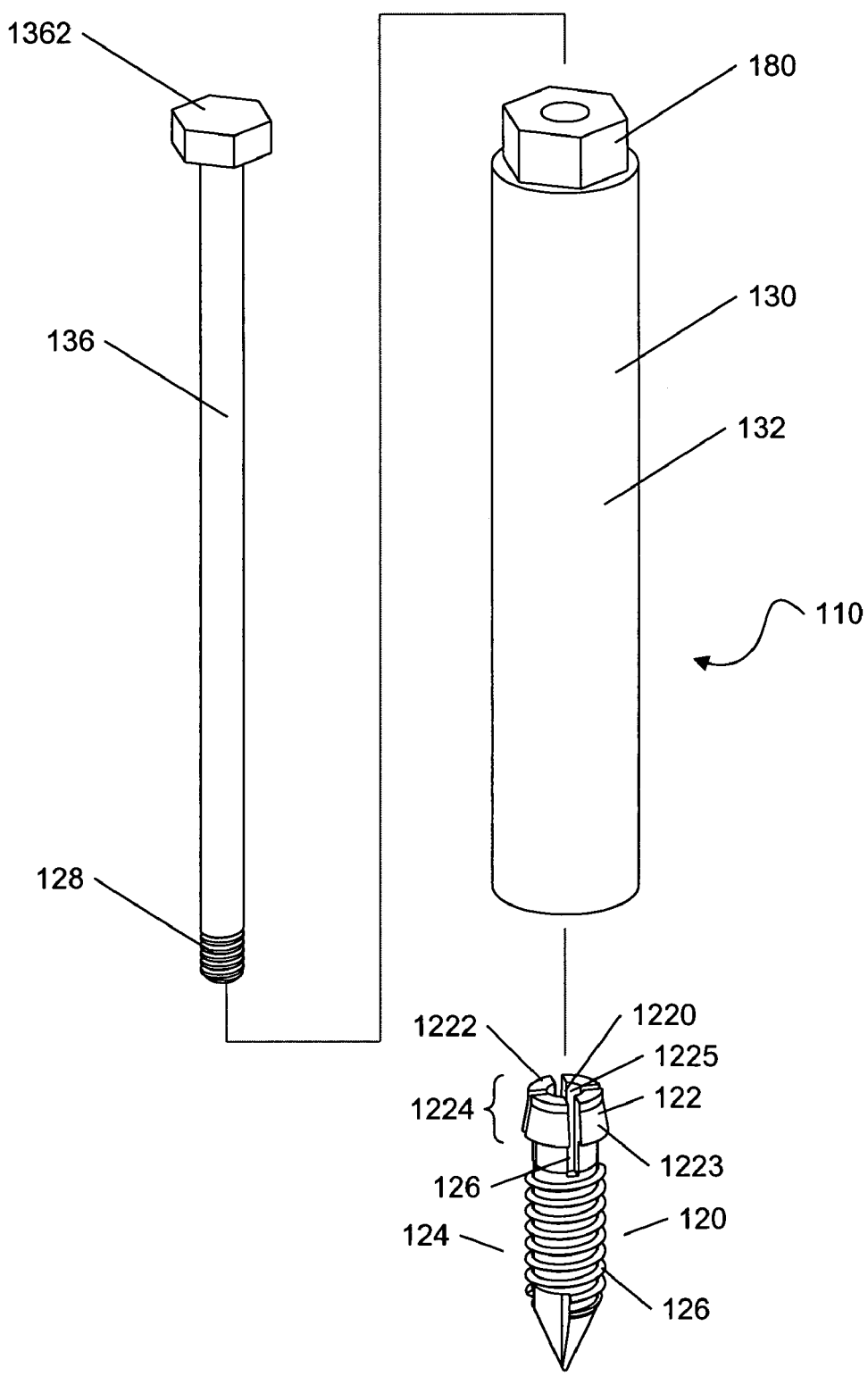

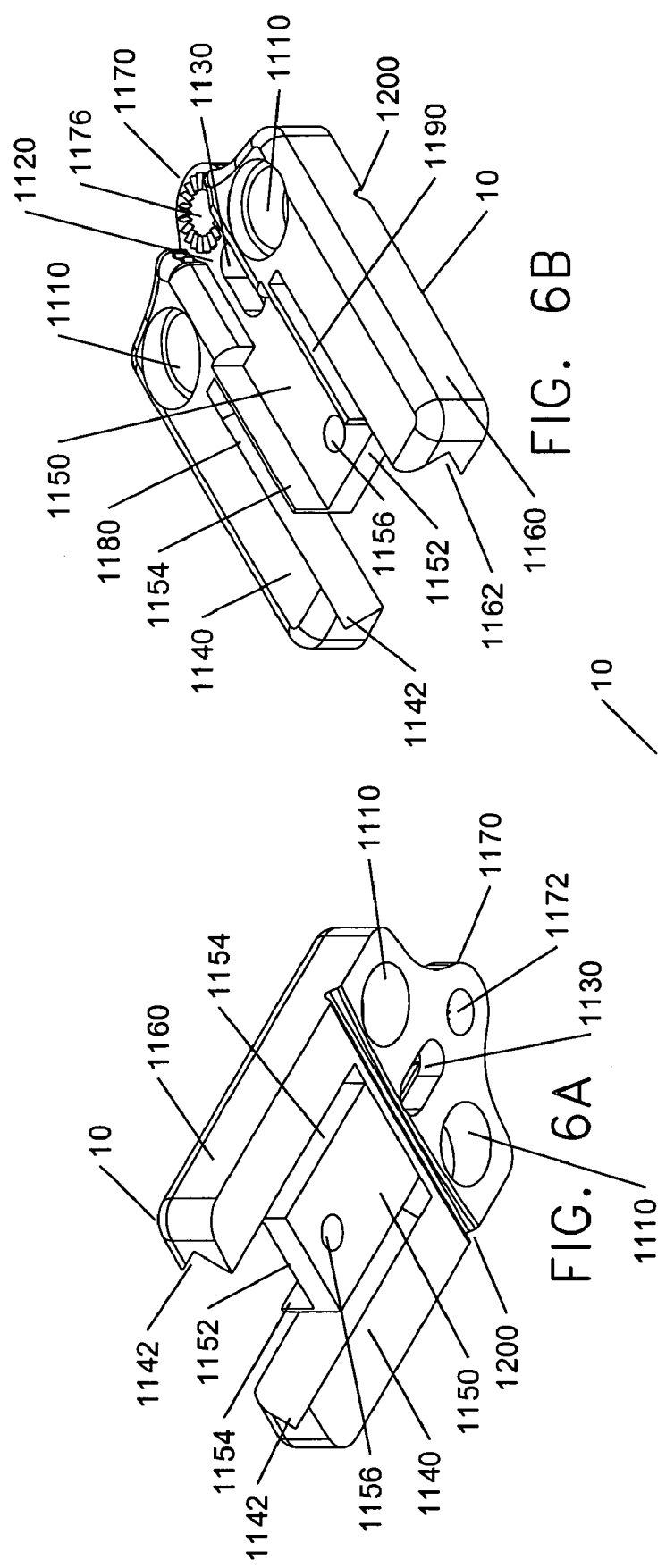
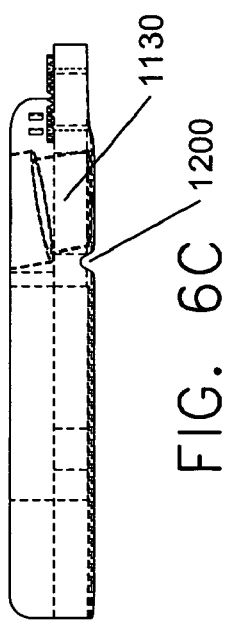

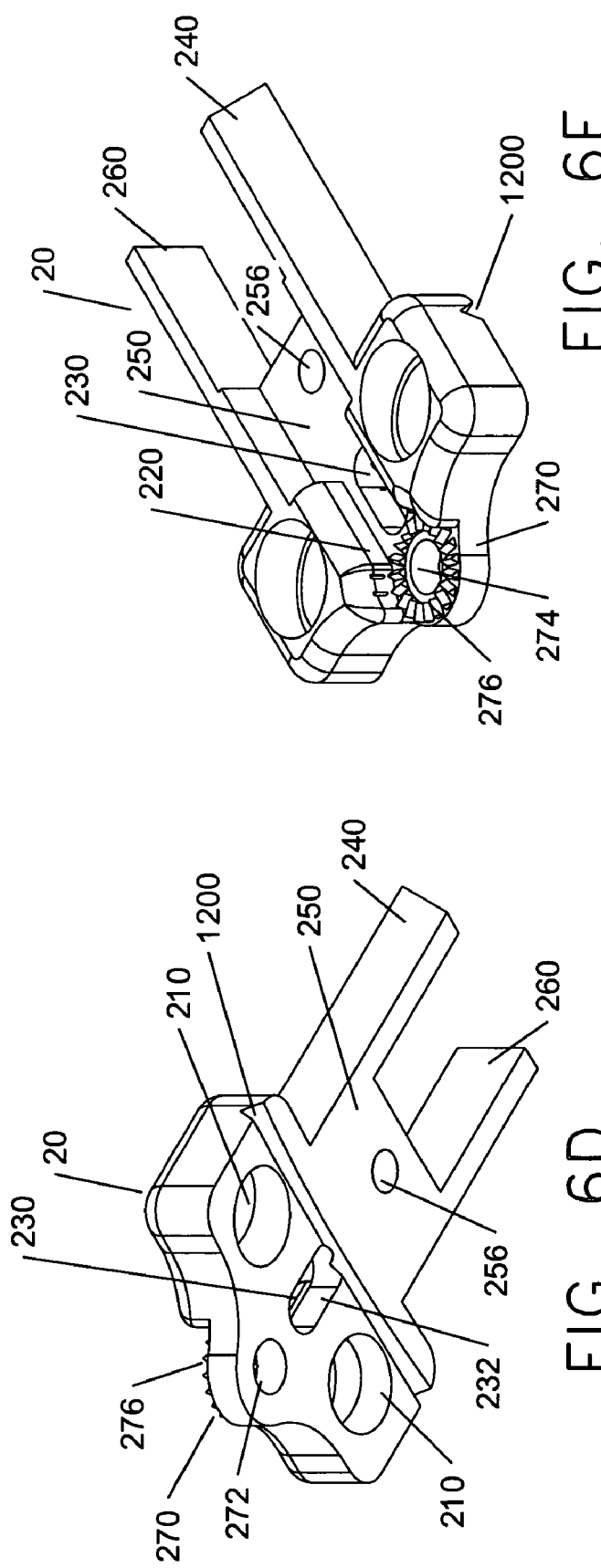
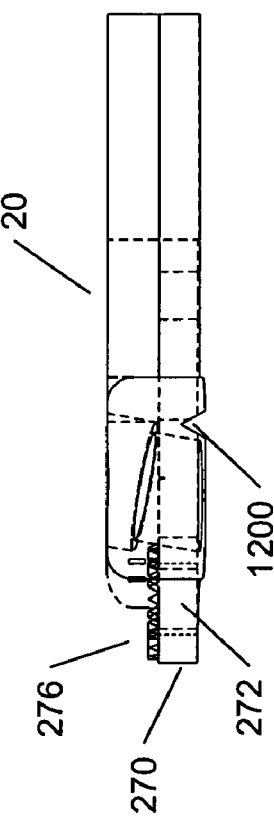
FIG. 6E
FIG. 6D
FIG. 6F

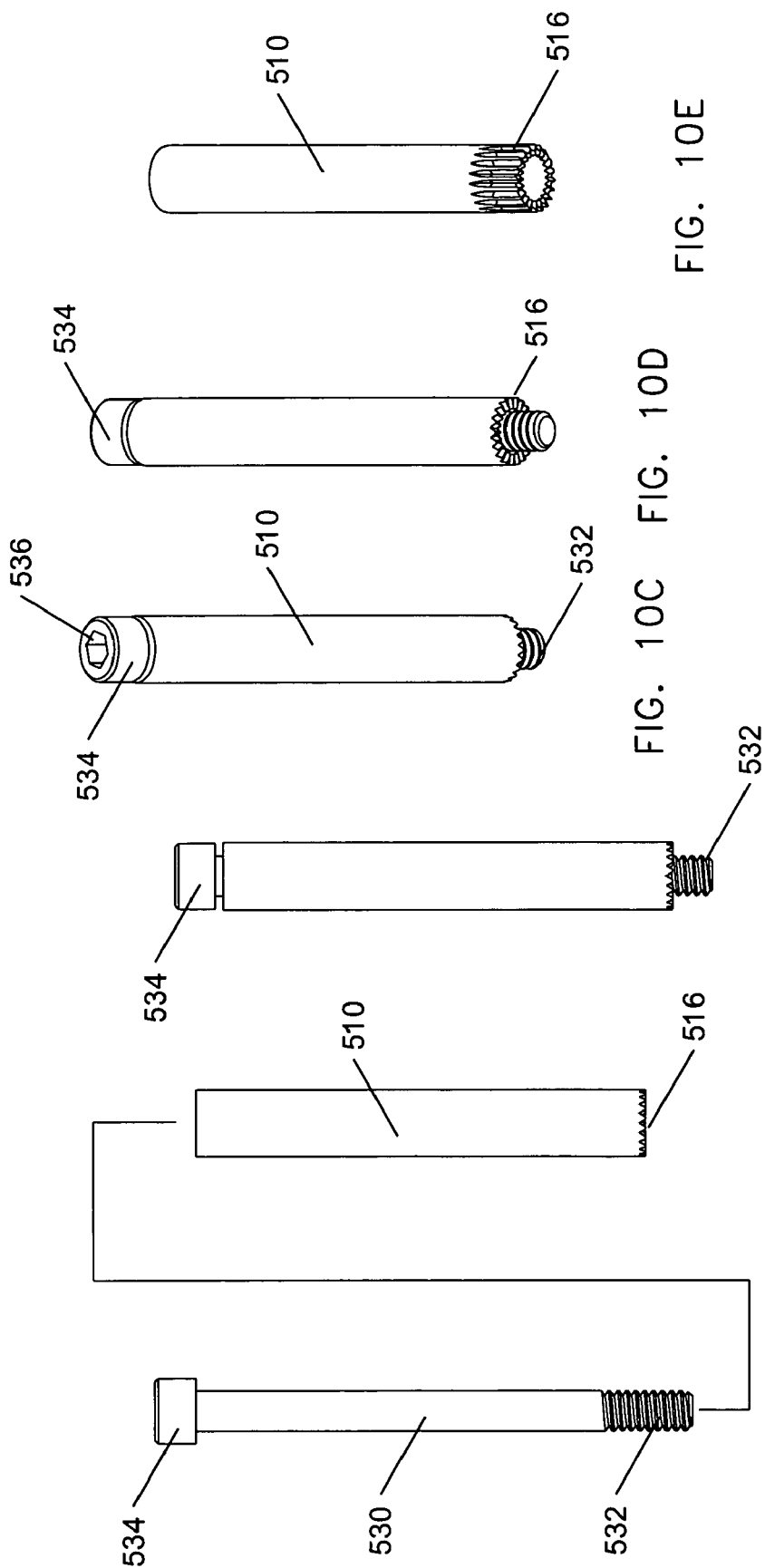

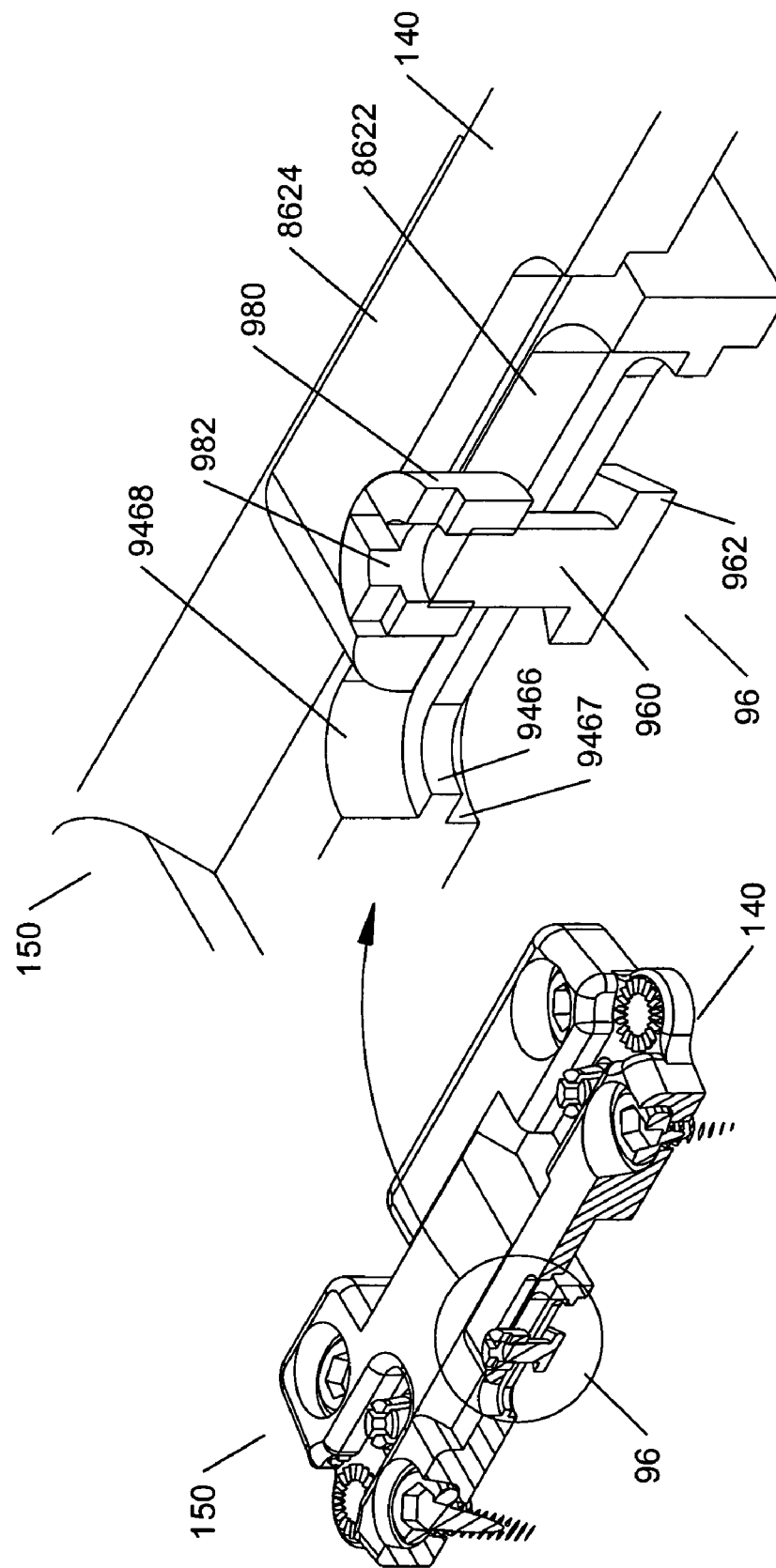

PLATING SYSTEM FOR BONE FIXATION AND SUBSIDENCE AND METHOD OF IMPLANTATION

RELATED APPLICATION

The present application claims priority to co-pending U.S. provisional patent application Ser. No. 60/439,030 filed on Jan. 10, 2003, and is a continuation-in-part of co-pending U.S. patent application Ser. No. 10/683,325 filed on Oct. 10, 2003, each of which is incorporated herein by reference in its entirety.

BACKGROUND

1. Field of the Invention

The present invention is directed at skeletal plating systems, components thereof, and method of implant placement. These systems are used to adjust, align and maintain the spatial relationship(s) of adjacent bones or bony fragments during healing and fusion after surgical reconstruction of skeletal segments. Such systems may be comprised of bone distraction devices, skeletal plates, bone screws and/or bone cables, bone screw-to-plate locking mechanisms, and any additional instruments needed for implant placement.

2. Related Art

Whether for degenerative disease, traumatic disruption, infection or neoplastic invasion, surgical reconstructions of the bony skeleton are common procedures in current medical practice. Regardless of anatomical region or the specifics of the reconstructive procedure, many surgeons employ an implantable skeletal plate to adjust, align and maintain the spatial relationship(s) of adjacent bones or bony fragments during postoperative healing. These plates are generally attached to the bony elements using bone screws or similar fasteners and act to share the load and support the bone as osteosynthesis progresses.

Available plating systems used to fixate the cervical spine possess several shortcomings in both design and implantation protocols. These plates are manufactured and provided to the surgeon in a range of sizes that vary by a fixed amount. This mandates that a large number of different size plates must be made and inventoried—adding to cost for manufacturer, vendor, and end user (hospitals). More importantly, the pre-manufactured sizes may not precisely fit all patients forcing surgeons to choose between a size too small or too large.

Plates used to attach three or more vertebrae after removal of two or more discs are manufactured with an equal distance between screw holes in the vertical plane. For example, the distance between the pair of C3 (cervical bone #3) and the pair of C4 (cervical bone #4) screws is equal to the distance between the C4 and C5 (cervical bone #5) screws as well as the distance between the C5 and C6 (cervical bone #6) screws and so forth. This not only ignores the known anatomical difference in size between bones at different levels but also fails to anticipate that a patient's unique pathology may require more extensive bony resection at one or more levels, further adding to these differences. Thus, selection of a plate with a suitable total length may still produce improper fit at one or more levels.

Current cervical plates are not modular, and will not permit addition of one plate to another for extension of the bony fusion at a future date. It is accepted that fusion of a specific spinal level will increase the load on, and the rate of degeneration of, the spinal segments immediately above and below the fused level. As the number of spinal fusion operations have increased, so have the number of patients who require extension of their fusion to adjacent levels. Currently, the original plate must be removed and replaced with a longer plate in order to fixate the additional fusion segment. This surgical procedure necessitates re-dissection through the prior, scarred operative field and substantially increases the operative risk to the patient. Further, since mis-alignment of the original plate along the vertical axis of the spine is common, proper implantation of the replacement plate often requires that the new bone screws be placed in different bone holes. The empty holes that result may act as stress concentration points within the vertebral bodies, as would any empty opening or crack within a rigid structural member, and lead to bone fracture and subsequent screw/plate migration.

Current plates may provide fixation that is too rigid. Since bone re-absorption at the bone/graft interface is the first phase of bone healing, fixation that is too rigid will not permit the bone fragments to settle and re-establish adequate contact after initial bone absorption. This process is known as "stress shielding" and will lead to separation of the bony fragments and significantly reduce the likelihood of bony fusion. Unsuccessful bone fusion may lead to construct failure and will frequently necessitate surgical revision with a second operative procedure.

Benzel (U.S. Pat. Nos. 5,681,312, and 5,713,900) and Foley (Pat. Applic. Pub. No. US2001/0047172A1) have independently proposed plating systems designed to accommodate bone settling. In either system, however, bony subsidence can be expected to cause one end of the plate to migrate towards an adjacent, normal disc space. This is highly undesirable since, with progressive subsidence, the plate may overlap the disc space immediately above or below the fused segments and un-necessarily limit movement across a normal disc space. Clearly, accommodation of bone settling at the plate's end is a sub-optimal solution.

Yuan et al described a multi-segmental plate consisting of two sliding parts in U.S. Pat. No. 5,616,142. While intended to be absorbable, this design may permit excessive play between the sliding segment and encourage bone screw loosening. In addition, this device does not permit application and maintenance of a compressive force across the bony construct. Baccelli noted these deficiencies in U.S. Pat. No. 6,306,136 and proposed a rigid plate capable of maintaining bony compression. However, the latter plate did not permit subsidence.

The implantation procedures of conventional plates in prior art practice have additional shortcomings. Distraction screws are used during disc removal and subsequent bone work and these screws are removed prior to bone plate placement. The empty bone holes created by removal of the distraction screws can interfere with proper placement of the bone screws used to anchor the plate and predispose to poor plate alignment along the long axis of the spine. This is especially problematic since the surgical steps that precede plate placement will distort the anatomical landmarks required to ensure proper plate alignment, leaving the surgeons with little guidance during plate implantation. For these reasons, bone plates are frequently placed "crooked" in the vertical plane and often predispose to improper bony alignment. Correct plate placement in the vertical plane is especially important in plates intended to accommodate bony subsidence, since the plate preferentially permits movement along its long axis. Thus, when the vertical axis of the plate and that of the spine are not properly aligned, the plate will further worsen the bony alignment as the vertebral bones subside.

The empty bone holes left by the removal of the distraction screws also act as stress concentration points within the vertebral bodies, as would any empty opening or crack within a rigid structural member, and predispose them to bone fracture and subsequent screw/plate migration. Improper plate placement and bony fractures can significantly increase the likelihood of construct failure and lead to severe chronic pain, neurological injury, and the need for surgical revision with a second procedure.

In view of the proceeding, it would be desirable to design an improved bone plating system and placement protocol. The new device should provide ease of use, reliable bone fixation, adjustable length, modular design, and the ability to accommodate and control bone settling. The design should also maximize the likelihood of proper plate placement and avoid maneuvers that weaken the vertebral bodies. No current plating system addresses all of these concerns. Therefore, what is needed is a system and method that overcomes these significant problems found in the conventional systems as described above.

SUMMARY

The present invention is that of a modular bone plate of adjustable length. The current invention provides a bone plate that permits maintenance of a compression force while also accommodating bony subsidence, among other features. A modular distraction screw is used for the bone work, including fusion, prior to plate placement. The distraction screw is placed as the first step of surgery when all relevant landmarks are still intact. After completion of the bone work, a proximal end of the distraction screw is detached, leaving a distal segment still implanted in the vertebral bodies above and below the newly fused disc space. The plate is guided to proper position along the upper and lower vertebra by the attached distal segments. The distal segments of the distraction screws are tightened onto the plate and the plate is held stationary while bone screws are placed.

The distal segments act as an anchor to guide the bone plate into the correct placement position and serve to hold the plate stationary while the plate's bone screws are placed. Since the distraction screws were placed with intact surgical landmarks, use of the distal segments to guide the plate significantly increases the likelihood of proper plate placement. In addition, the distal segments of the distraction screws serve as additional points of fixation for the plate and leave no empty bone holes which give rise to stress concentration points that further weaken the vertebral bodies.

After the plate is attached to the upper and lower vertebras, the plate is set to the desired length and the two segments are locked together. If application of a compressive force is desired, the plate can be used to maintain the force across the vertebral bodies by simply locking the plate segments after applying compression. Occasionally, surgeons are confronted with a grossly unstable spine from the patient's unique pathology and choose to forgo subsidence in favor of a more fixed and rigid construct. In these situations, plate placement is essentially complete and requires no further steps. More commonly, subsidence is desired and release of a second locking screw permits the plate to accommodate bony subsidence. Unlike current plating systems which provide either a rigid plate or one capable of subsidence, the current invention permits either option by the simple turn of one screw. Further, when subsidence is chosen, this plate will not overlap the adjacent disc space with bone movement, since subsidence is accommodated at the level of settling bone and not at the plate's end.

Extension of the fusion at a later date is easily accomplished without plate removal. An adapter is placed at either end of the plate that can couple with either a modified distraction screw or an additional bone plate. Fusion extension is started by connecting a modified distraction screw to the coupler at-the end of the plate immediately adjacent to the disc to be removed. A modular distraction screw is inserted into the adjacent vertebra and a discectomy and subsequent fusion are performed within the intervening disc space. After completion of the bone work, the modified distraction screw is removed leaving the bare coupler on the end of the plate. The proximal segment of the distraction screw is also removed leaving the distal segment attached to the adjacent vertebral body. An extension plate is used to span the space between the distal segment of the distraction screw on the adjacent vertebra and the end-coupler on the original plate. In this way, the fusion is extended and the newly fused segment is fixated without removal of the original plate. Further, the end-coupler can used to correct for any improper ("crooked") placement of the original plate by rotating the extension plate into the true vertical.

The preceding discussion has focused on removal of one disc with fusion and plate fixation of the vertebral bodies above and below the evacuated disc space. However, "multilevel" procedures (that is, removal of two or more discs and fusion of three or more bones) can also be addressed with this system. Removal of two or more discs is accomplished by the step-wise removal of individual discs until all pathological levels have been addressed. Modular distraction screws may be used at each vertebral level if desired, but their use is required only at the upper and lower-most vertebras while conventional distraction screws can be used at all intervening levels. After completion of the bone work, the proximal segments of the distraction screws are removed leaving the distal segments attached to the upper and lower-most vertebral bodies. Regardless of the type of distraction screw used at the other levels, that screw is completely removed after the completion of the bone work. The empty bone holes left at these intervening level are far less important than those produced at the upper and lower-most vertebra, since the latter share a disproportionate share of the load.

In one embodiment of the present invention, plates used for multi-level procedures will have an expandable/subsidence mechanism overlying each disc space that is fused. The plate is guided to proper position along the upper-most and lower-most vertebra by the attached distal segments—as described above for single level procedures. The distal segments of the distraction screws are tightened onto the plate and the plate is held stationary while bone screws are placed into the upper and lower-most vertebras. In this way, the plate is fixed at each end. Depending on surgeon preference, fixation of the intervening vertebral levels may be started from either end of the plate. For illustration, fixation will be started inferiorly. The plate segment intended to fixate the vertebra immediately superior to the lower-most vertebra is moved into optimal position. The sliding mechanism between this segment and the plate segment attached to the lower-most vertebra is then locked, fixing these two segments together. Bone screws can then be easily and rapidly placed into the vertebra immediately superior to the lower-most vertebra. The process is repeated at each of the remaining vertebra. If compression is desired across the construct, it's applied across the upper and lower-most vertebras prior to placement of the bone screws into any of the intervening vertebra. Compression is maintained until all the vertebra have been fixed to the plate. Once all sliding mechanisms have been locked, the compression device may be released and the force will be maintained by the plate. If a rigid construct/plate is desired, then plate placement is complete. However, if subsidence is needed, the (subsidence) locking screw is opened at each level where bone subsidence is desired. In this way, this plate design permits the surgeon to choose the exact vertebral levels to fixed rigidly and those level that will be allowed to accommodate subsidence. Further, it permits the distance between the bone screws at different levels to be custom fit for the individual patient. These features are not shared by any currently available plating system.

In other embodiments, multi-level plates will be designed without a sliding/subsidence mechanism at every level. Instead, one or more sliding/subsidence mechanism(s) will be used to affect two or more levels by use of a slotted borehole configuration between levels. At each end, however, the plate will remain rigidly fixed to bone. In this way, subsidence continues to be accommodated at the level of bony movement and the plate remains stationary at each end.

All embodiments of the multi-level plates will preferentially, but not necessarily, contain central channels to accommodate the distal segment of the modular distraction screw and end-couplers so that extension of the fusion at a future date remains possible.

In other embodiments of the present invention, additional plate design, different locking mechanisms, and alternative end couplers are shown and described. Other embodiments, in addition to those illustrated, can also be used.

The plating systems described in the present invention provide ease of use, reliable bone fixation, adjustable length, modular design, and the ability to accommodate and control bone settling. These designs will also maximize the likelihood of proper plate placement, avoid maneuvers that weaken the vertebral bodies, and provide a significant advantage over the current and prior art. These and other features of the present invention will become more apparent from the following description of the embodiments and certain modifications thereof when taken with the accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is a partial side view of a disassembled distraction screw according to an embodiment of the invention;

FIGS. 6A-6F are top, bottom, and side views of angled bracket plate components according to an embodiment of the invention;

FIG. 10A is a partial side view of a modified disassembled distraction screw according to an embodiment of the invention;

FIGS. 10B-10D are partial side views of a modified assembled distraction screw according to an embodiment of the invention;

FIG. 10E is a close up view of a modified distraction screw according to an embodiment of the invention;

FIG. 13A is a sectional view of a bone plate according to an embodiment of the invention;

FIG. 13B is a close up sectional view of the locking mechanism of a bone plate according to an embodiment of the invention;

DETAILED DESCRIPTION

Certain embodiments as disclosed herein provide for a modular bone distraction screw and a modular bone fixation plate with an adjustable length to accommodate bone settling. For example, one plating system disclosed herein allows for compression to be set during placement of the plate and also allows subsidence of the bone while maintaining the initial compression.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 2:
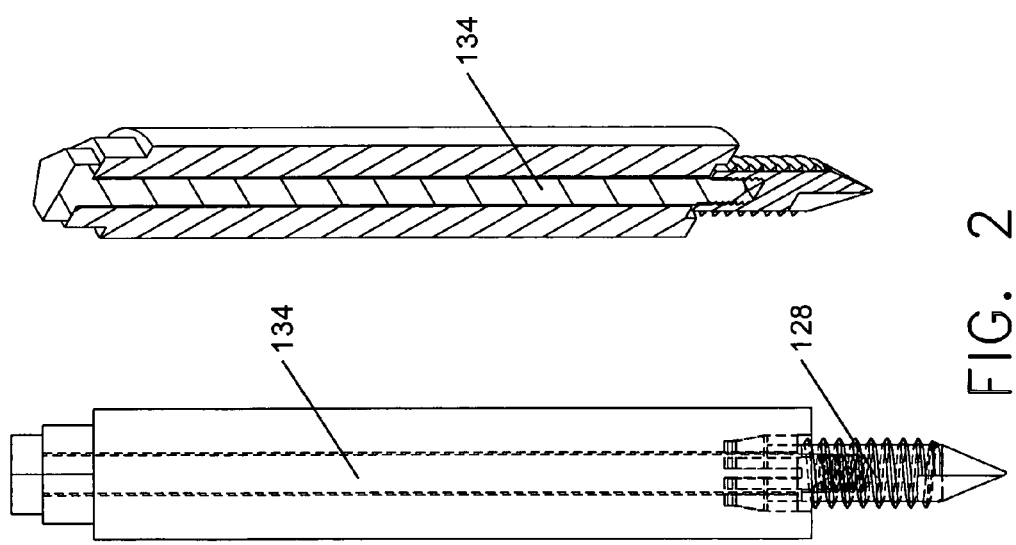
FIG. 2 is an assembled distraction screw and a cross sectional side view of the assembled distraction screw according to an embodiment of the invention.

FIG. 1 shows a modular distraction screw 110, which comprises a distal segment 120 and a removable proximal 130 segment. The distal segment 120 has a head portion 122, and a threaded shank portion 124, which can be securely fastened unto bone. The proximal segment 130 comprises an elongated body 132 and deployable member 136. Elongated body 132 has a smooth-walled internal bore 134 extending through its full length and houses the deployable member 136 within the bore. The deployable member 136 is adapted to be retractably deployed beyond the distal end of the internal bore 134. FIG. 2 shows the assembled distraction screw.

FIG. 3 illustrates distal segment 120, which comprises a threaded shank portion 124 and a head portion 122. Threads 126 of the shank portion 124 are preferably self-tapping and/or self-drilling. Depending on the particular application, the shank 124 can be of variable lengths and diameter. In one application, the outer diameter of the shank/threads is preferably equal to the widest point of head 122. One of ordinary skill in the art would understand that the threads can be of any design that is well known to be applicable for screwing placement into mammalian bone.

Figure 3B:
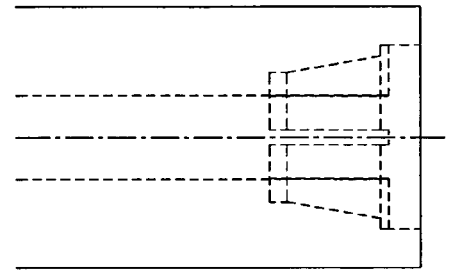
FIGS. 3A-3B are close up views of the connector portion of the elongated body of a distraction screw according to an embodiment of the invention.
Figure 3A:
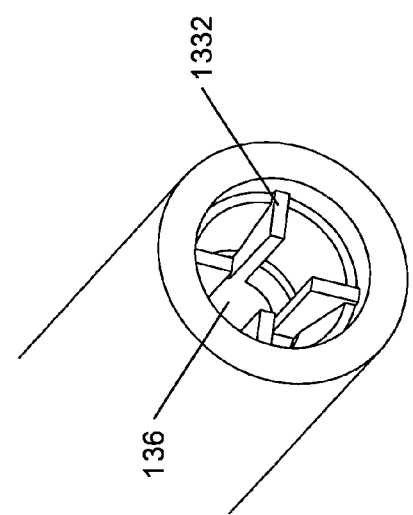

Head 122 is circular with hollow central bore 1220. The upper aspect 1222 of the circular head is of uniform diameter but the lower portion 1223 of the head is of progressively greater diameter such that the head has a sloping side wall below edge 1224. Threads 1225 are located within bore 1220 and are complementary to threads 128 of deployable member 136. Head 122 has a plurality of slots 1226 which are engageable by projections 1322 of the distal aspect of elongated body 132, as shown in FIG. 3A and FIG. 3B. Slots 1226 permit the head to collapse inward when centripetal force is applied to the outer wall of the head.

Deployable member 136 is advanced through bore 134 to engage distal segment 120 with the coupling of the complimentary threads 128 and 1225. The proximal head 1362 of member 136 permits application of rotational force to deployable member 136 (as shown in FIG. 2) further driving threads 128 and 1225 together and locking members 132, 136 and distal segment 120 together. While depicted as a hex configuration, any engagable configuration may be used to drive deployable member 136.

The coupled proximal segment 130 and distal segment 120 employing the above-described means of engagement provide a modular distraction screw. When fully assembled, the screw functions as a unitary device. In a surgical application, a wrench (not shown) is attached to the tool attachment portion 180 of elongated member 132 (FIG. 1), and the distraction screw is positioned at a site of a bone. A rotational force is applied to portion 180 causing the proximal and distal segments to rotate in unison so that thread 126 of the distal segment 120 engages the underlying bone and shank 124 is advanced into the bone.

After the distraction screw is used to perform the bone work, the proximal segment 130 is detached from distal segment 120. The distraction screw is disassembled into its components by applying a rotational force to head 1362 of member 136 in a direction opposite (usually counter-clockwise) to that required for screw assembly (usually clockwise). The distal segment is held stationary while threads 128 and 1225 are disengaged by applying a counter force to distal segment 120 using the proximal portion 180 of the elongated body 132. In this way, the proximal segment 130 is removed leaving the distal segment 120 attached (implanted) to the bone structure.

As implanted, the distal segment 120 provides enhanced structural integrity of the bone by reducing the stress concentration generally expected of an empty opening in a structural member. In addition, leaving the distal segment 120 attached to bone eliminates the robust bone bleeding encountered after removal of current, commercially-available distraction screws and obviates the need to fill the empty hole with a hemostatic agent.

The distal segment 120 also provides a point of anchoring for a skeletal plate and help insure proper plate placement. Since placement of the distraction screws is performed as the first step in the surgical procedure, the anatomical landmarks required to ensure proper alignment of the plate in the desired anatomical plane are still intact.

Alternatively, a conventional one-piece distraction can be used to distract the vertebra during discectomy. After the bone work is finished, the conventional distraction screw is removed leaving an empty bone hole. A distal segment 120 is placed into the empty bone hole and provides an anchor point for the skeletal plate.

Figure 5A:
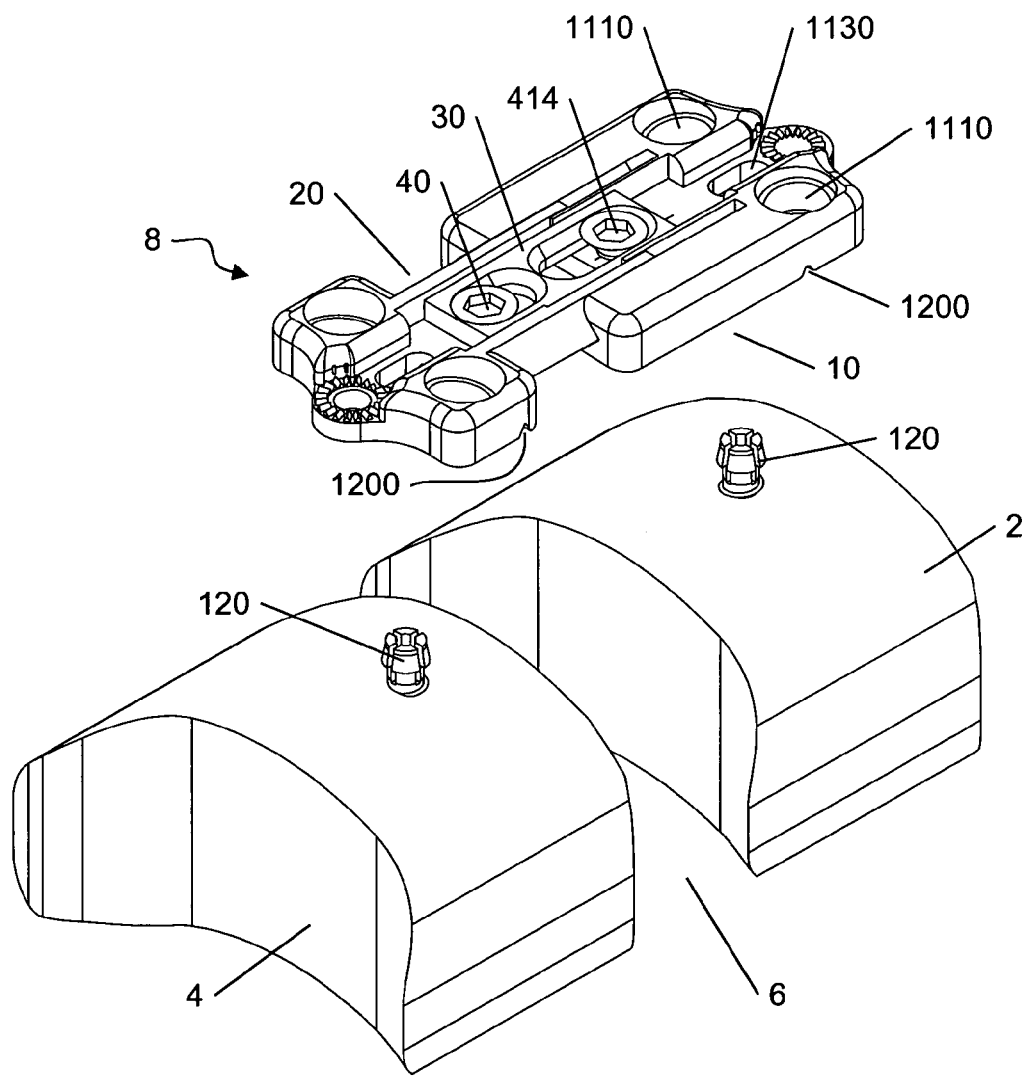
FIGS. 5A-5B are exploded perspective views of a bone plate according to alternative embodiments of the invention.
Figure 5B:
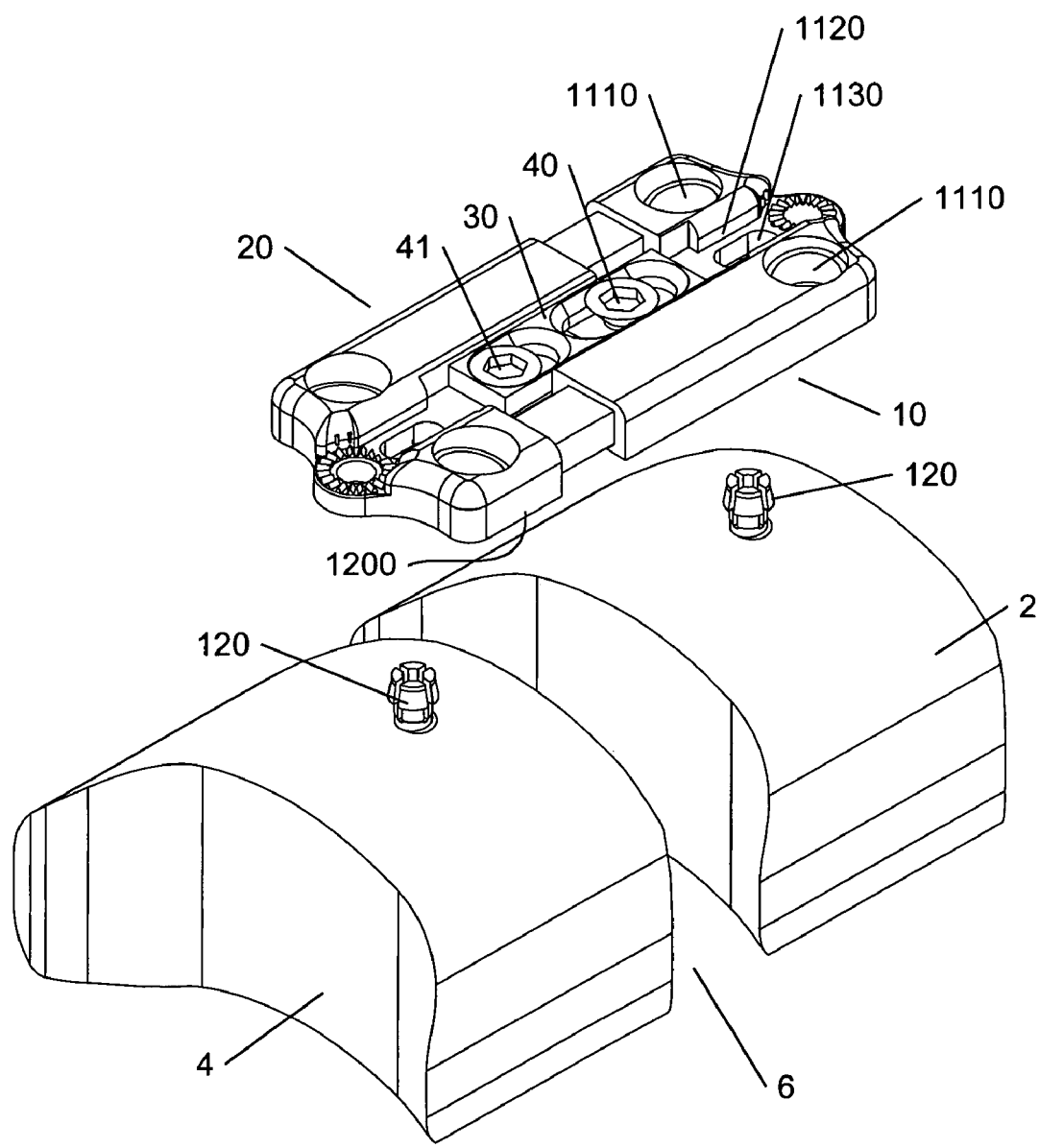
Figure 5C:
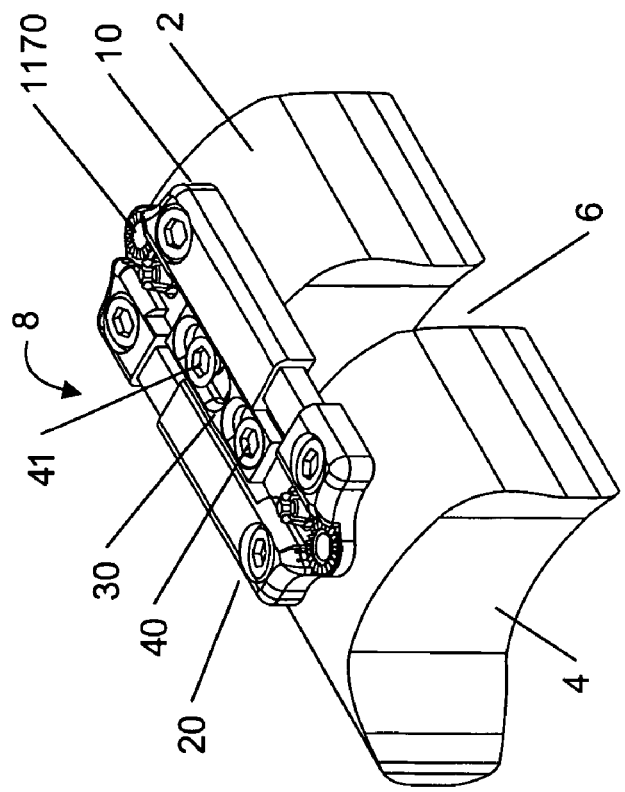
FIGS. 5C-5D are perspective views of a mounted bone plate according to alternative embodiments of the invention.
Figure 5D:
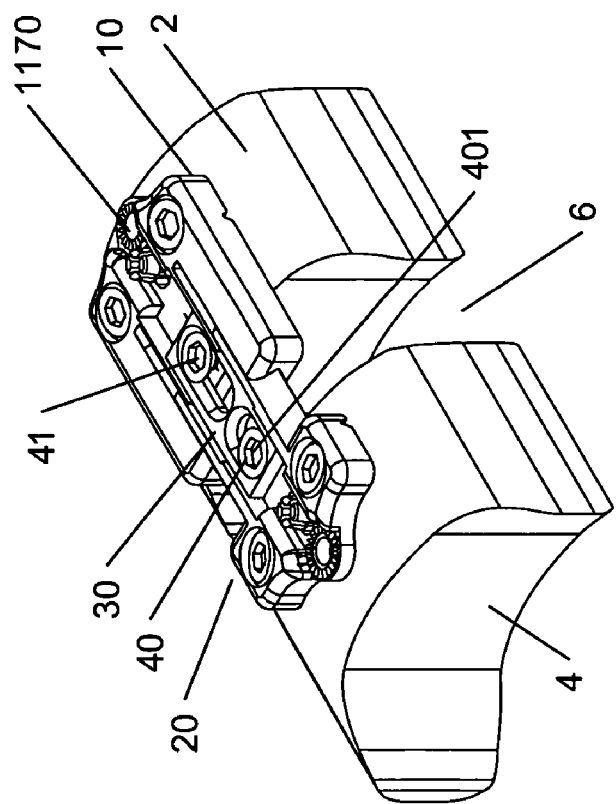
Figure 7B:
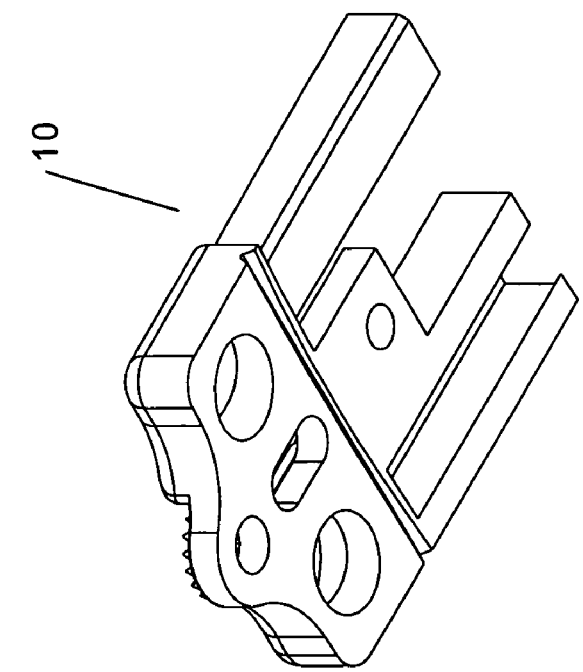
FIG. 7A-7C are top, bottom, and side views of square bracket plate components according to an embodiment of the invention.
Figure 7C:
Figure 7A:
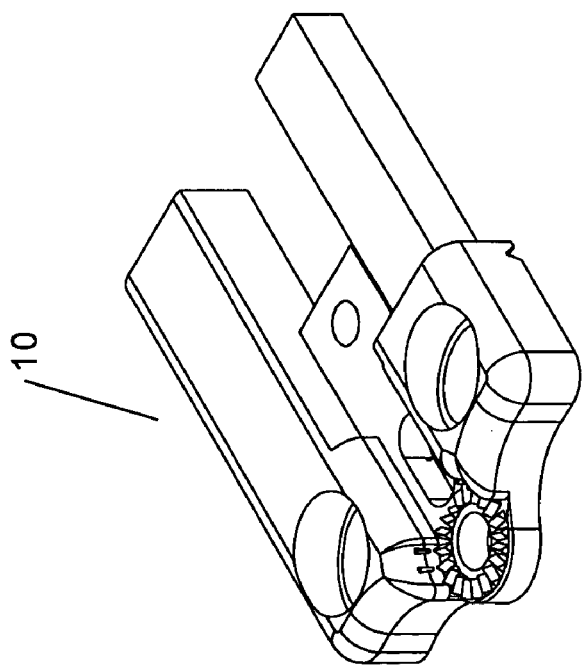

FIGS. 5A and 5B show two vertebral bodies 2 and 4 and the plating system 8 of the present invention used to fixate them. The plating system includes sliding plate segments 10 and 20 and a coupler means or a coupler segment 30, which couples the sliding segments 10 and 20 and controls their movements. FIGS. 6-7 show the top and mid-sectional views of the embodiment of the bone fixation plate.

The plate segments 10 and 20 may be curved in either the vertical or horizontal plane in order to conform to the shape of the bone it is designed to fixate. For example, plates designed to attach onto the anterior aspect of the cervical spine are preferentially, but not necessarily, convex in both the vertical and horizontal planes. Further, the plate surface immediately adjacent to the bone surface may contain one or more horizontal indentations 1200 in order to permit the placement of additional curvature in the vertical plane.

The plating system or any of its components can be made of any biologically adaptable or compatible materials. Materials considered acceptable for biological implantation are well known and include, but are not limited to, stainless steel, titanium, combination metallic alloys, various plastics, resins, ceramics, biologically absorbable materials and the like. It would be understood by one of ordinary skill in the art that any system component can be made of any materials acceptable for biological implantation and capable of withstanding the torque required for insertion and the load encountered during use. Any components may be further coated/made with osteo-conductive (such as demineralized bone matrix, hydroxyapatite, and the like) and/or osteo-inductive (such as Transforming Growth Factor "TGF-B, " Platelet-Derived Growth Factor "PDGF," Bone-Morphogenic Protein "BMP," and the like) bio-active materials that promote bone formation. Further, any instrument or device used in implant placement may be made from any non-toxic material capable of withstanding the load encountered during use. Materials used in these instruments need not be limited to those acceptable for implantation, since these devices function to deliver the implatable segments but are not, in themselves, implanted.

As shown in FIGS. 5-7 sliding segment 10 has two boreholes 1110 which are formed through the plate to accommodate fastening elements, such as bone screw. Each borehole may be oriented in the true vertical plane or form an angle with the vertical. For use in the cervical spine, boreholes 1110 will preferentially, but not necessarily, be angled towards each other in the horizontal plane and away from the sliding end in the vertical plane. The top opening of the boreholes may be flush with the plate surface or may be recessed. The distance between the boreholes may also vary depending on the requirement of plate application and design. A depression 1120 is present between the boreholes with slot 1130 along the depression. The side walls 1132 of slot 1130 are preferentially, but not necessarily, angled with the true vertical such that the top opening of slot 1130 is slightly smaller than the bottom opening. Slot 1130 is adapted to accommodate or mate with screw head 122 of distal segment 120 of the distraction screw. While depicted as an elongated hole, slot 1130 may alternatively be a circular hole.

Plate segment 10 has three projections, consisting of two side projections 1140, 1160 and a central projection 1150. Two indentations 1180 and 1190 are formed between these three projections. The inside wall of each projection 1140 and 1160 contain indentations 1142 and 1162, respectively. While depicted as "V" shaped, these indentations may be made of any geometric configurations including, but not limited, square, oval, circular, and hybrid designs which are complimentary to the sliding portion of the other plate segment 20. The central projection 1150 has a partial thickness middle segment 1152 and two full side walls 1154. An opening 1156 with internal threads 1158 is provided on segment 1152. The top surface of middle segment 1152 is preferentially textured so as to permit superior contact with the undersurface of the complementary plate component.

The other end portion of the plate segment 10 has a projection 1170, which is preferentially, but not necessarily, position in the midline of the plate segment. The projection has a central hole 1172 with threads 1174. Spines 1176 may be placed along the top of the projection to mate with complimentary spines on the add-on attachments, as shown in FIG. 4. These spines may be placed on any one or combination of surfaces adjacent projection 1170. These surfaces may be textured or left smooth.

FIGS. 6D, 6E, 6F & 7 illustrate the complementary sliding plate segment 20 to sliding segment 10. Again, two boreholes 210 are vertically formed through the plate to accommodate fastening elements. As with sliding plate segment 10, these boreholes may be oriented in the true vertical plane or form an angle with it, may be flush with the plate surface or further recessed, and the distance between these holes may vary depending on the requirement of the plate application. A depression 220 is formed between the boreholes with a slot 230 whose side walls 232 are preferentially angled with the true vertical such that the top opening of the slot is slightly smaller than the bottom opening. Slot 230 is adapted to mate with and accommodate the distal segment of a distraction screw.

Sliding plate segment 20 has two projections 240, 260 and central connection 250. Projection 240 has an extension 242 which is complementary to indentations 1142 of projections 1140. Likewise, projection 260 has an extension 262 that is adapted to be received by indentations 1162 of projection 1160. Projections 240 and 260 may be of any geometric configuration and cross-section including, but not limited, square, oval, circular, truncated triangular, modified rectangular and hybrid designs that are complimentary to the corresponding sliding portions of the segment 10. Further, projections 240 and 260 may be of differing designs that are complimental to projections 1140 and 1160. The central connection 250 has a partial thickness middle segment 252 and two side walls 254. An opening 256 with internal threads 258 is located on segment 252. Openings 256 and 1156 may be aligned with the direction of bone subsidence.

On its opposite end, plate segment 20 has a partial thickness projection 270 that is preferentially, but not necessarily, in the midline of the plate. Projection 270 has a central hole 272 with threads 274. Spines 276 may be placed along the top of the projection to mate with complimentary spines of the add-on attachments. These spines may be placed on any one or combination of surfaces adjacent projection 270. These surfaces may be textured or left smooth.

Figure 8B:
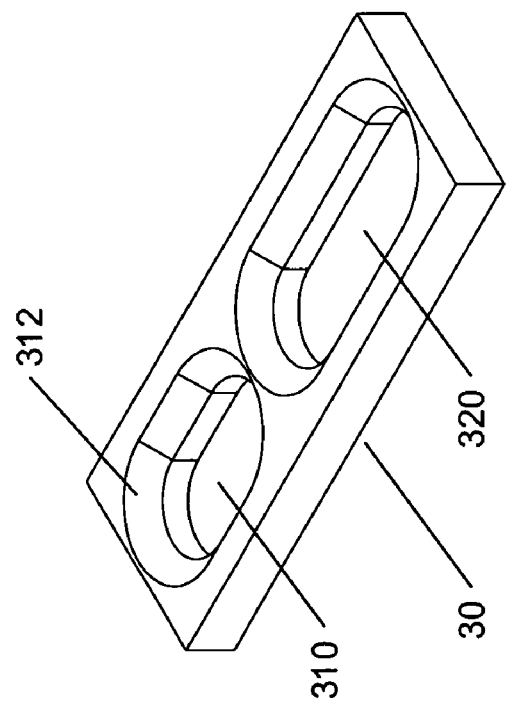
FIGS. 8A-8B are top views of a third plate component according to an embodiment of the invention.
Figure 8A:
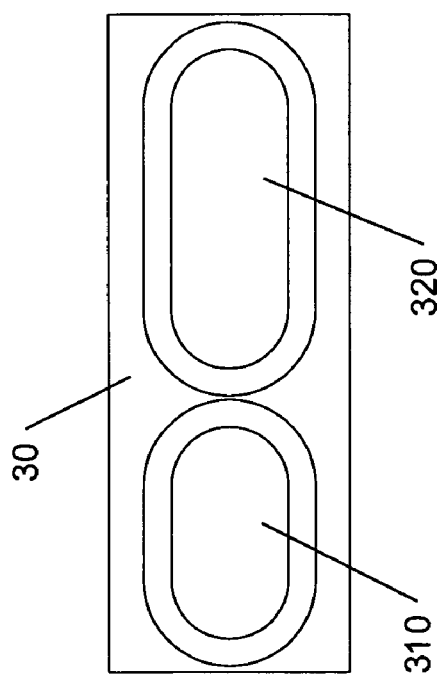

FIG. 8 illustrates top and oblique views of coupling means or segment 30. Two full thickness channels 310 and 320 are formed within segment 30. The channels are preferentially, but not necessarily, of different lengths and walls 312 and 322 of channels 310 and 320 are preferentially angled with the vertical plane. The top surface of coupling segment 30 is smooth while the bottom surface is preferentially textured in the portion of the segment with the larger channel 320. The bottom of the segment with the smaller channel 310 is smooth. Coupling segment 30 couples plate segments 10 and 20 as depicted in FIG. 5 with screws 40 and 41. While not depicted, each screw has threads on which are complimentary to threads 158 of segment 10 and threads 258 of segment 20. The screws have top depressions 414 and 404 for engagement by a screwdriver or other driving instrument. While both screws are depicted as being identical, each may be of any of the many well known fastener designs and may be inserted using any complimentary driver.

Projections 1150 and 250 of sliding plate segment 10 and 20 respectively may be of equal or different lengths. When unequal, central projection 1150 is made longer than projection 250 as a matter of preference. (Alternatively, the longer projection may be placed within segment 20.) The longer channel 320 of segment 30 engages the longer central projection (element 1150 of segment 10) by screw 41 while the shorter channel 310 engages the shorter central projection (element 250 of segment 20) by screw 40.

The bone screws and the screw for the coupler segment 30 may be of any of the many well known designs considered acceptable for implant attachment to the bony skeleton and made from any material intended for biological implantation.

As an option, any portion of the plating segments may be made of radiolucent materials (such as PEEK, PEAK, and the like) so that unfettered x-ray examination of the underlying bone can be performed in the post-operative period. Thus, projections 1150, 250 and segment 30 can be made from radiolucent materials so as to provide a window for x-ray examination of the bone without decreasing the overall strength of the plate.

After completion of the bone work and detachment of the proximal portions of the distraction screws, the distal segments are left attached to the vertebra above and below the newly fused disc space. The bone plate is fully assembled before implantation. Screw 40 is fully seated at the outside edge 312 of channel 310 so that plate segment 20 and coupler segment 30 are fixed relative to one another. However, screw 41 is partially seated on the outside edge 320 of channel 320 so that plate segment 10 and coupler segment 30 are free to slide relative to each other. Slot 1130 and 230 are aligned with the distal segments 120 which are implemented on the bone structure following bone work upon which the heads 122 of distal segments 120 are snapped into the slots. As the head 122 spring back, the plate segments are held between the screw heads 122 and the underlying bone 2 and 4.

Figures 4A, 4B:
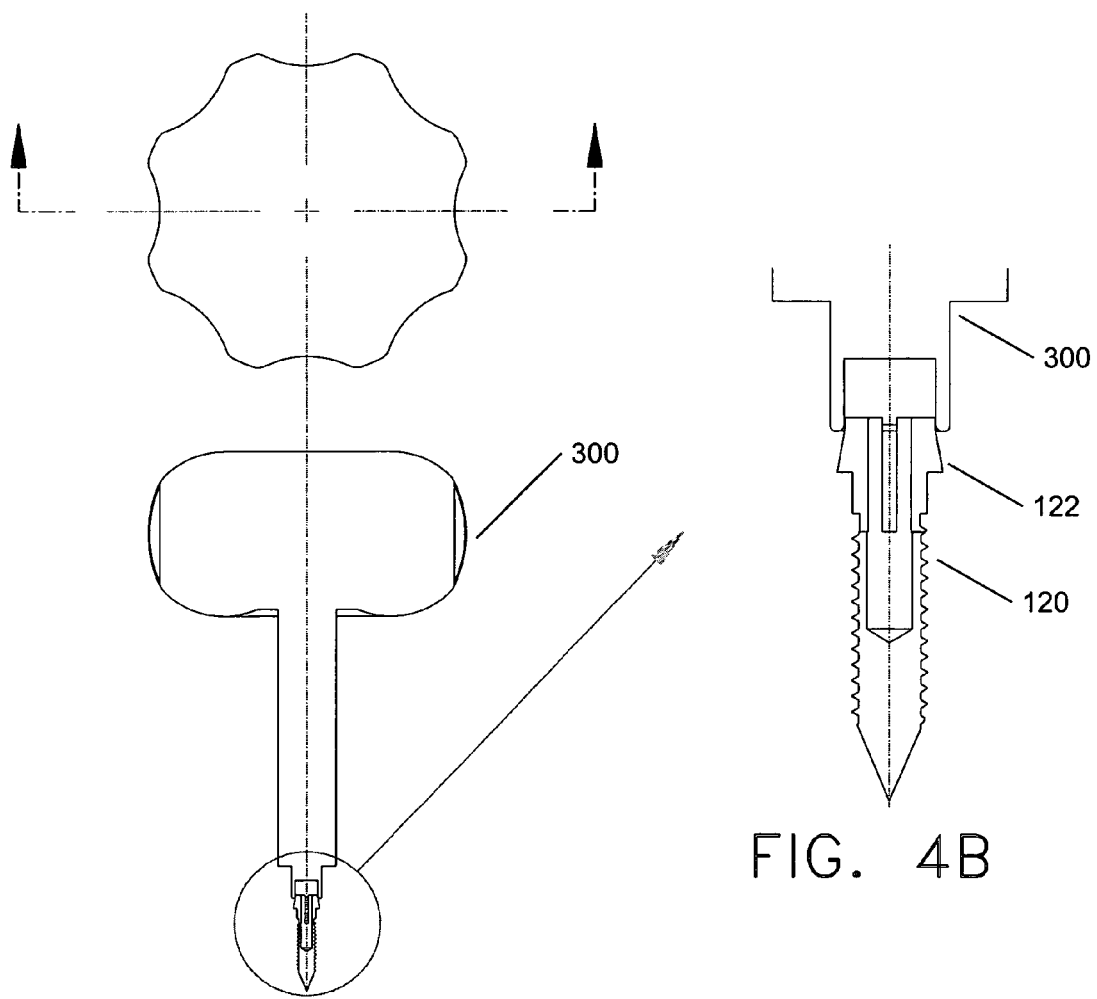
FIGS. 4A-4B are partial views of a distraction screw removal tool according to an embodiment of the invention.

If the plate is poorly positioned because of bony irregularity, it can be removed to permit additional bone work. FIGS. 4*a* & 4*b* illustrate a screw head remover 300, which can be used to remove the plate segments. When pushed onto head 122 of distal segment 120, the screw head remover applies a centripetal force to the side walls, causing them to move inward, and permitting plate removal. Alternatively, if the plate is well positioned, the boreholes are moved into optimal position for bone screw placement. A screw driver is used to drive distal segment 120 further into the bone, thereby holding the plate stationary. The bone screws are then easily placed into the underlying bone.

Once the plate segments are set to the desired length, screw 41 is tightened. If desired, compression can be placed across the bony construct and maintained with closure of screw 41. The inferior surface of segment 30 around the longer channel 320 and the superior surface of projection 1150 is preferentially, but not necessarily, textured so as to promote greater frictional contact between segments 10 and 30. At this point, the plate is rigid. If accommodation of bony subsidence is desired, screw 40 is unlocked, permitting movement of segments 20 towards each other as bone settling occurs. The extent of subsidence permitted is governed by the length of channel 310.

Figure 9B:
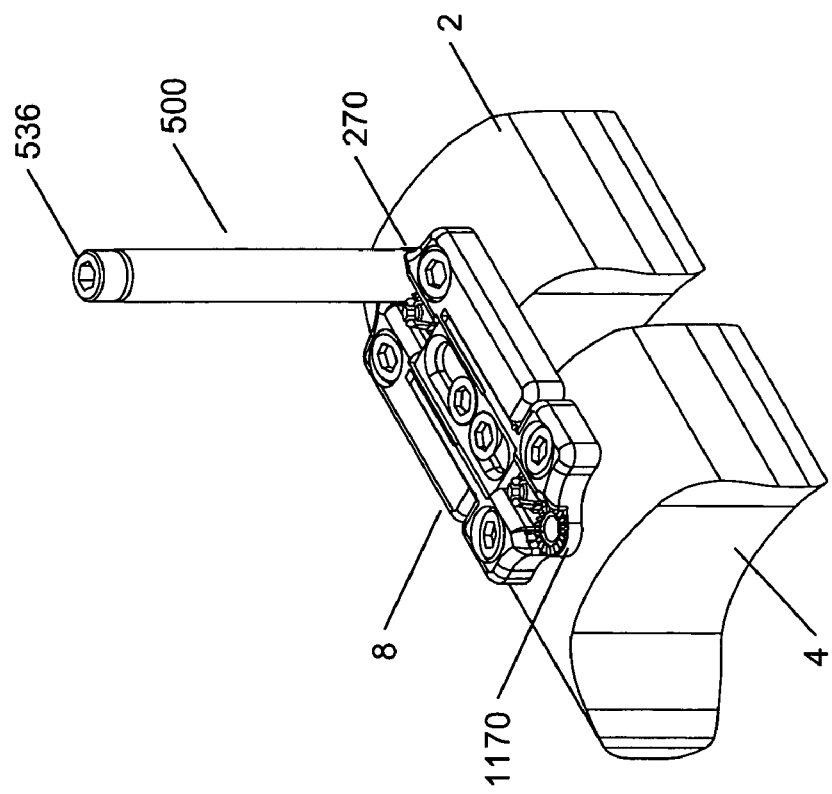
FIGS. 9A-9B are perspective views of a modified distraction screw attached to a bone plate according to an embodiment of the invention.
Figure 9A:
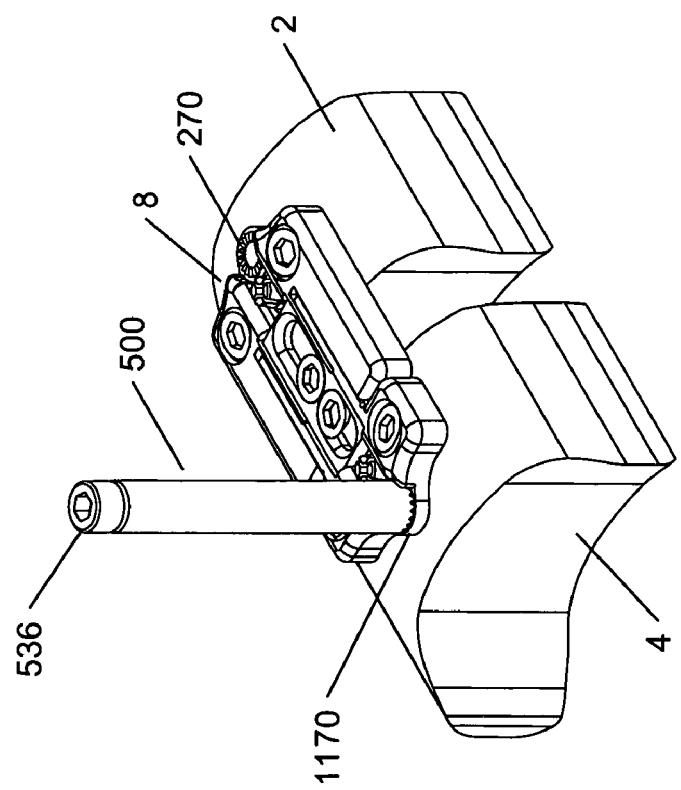

Extension of the fusion at a future date can be easily accomplished without plate removal. Incorporation of the vertebral body immediately above or below into the fusion mass is started by placement of a modular distraction screw 110 into that adjacent vertebra. A modified distraction screw is used to engage the end-coupler of the existing plate as shown in FIG. 10. As shown in FIGS. 9, 10 and 11, the modified distraction screw 500 comprises an elongated body 510 with an internal bore 512 extending through its entire length to distal end portion 516. The elongated body 510 houses a deployable member 530, which is disposed within the internal bore 512. The deployable member 530 is adapted to be retractably deployed beyond the opening 516 of internal bore 512. Threads 532 are located on one end of member 530 and head 534 is formed on the other end. Head 534 has diameter greater than that of the internal diameter of bore 512. Depression 536 is formed within head 534 so as to permit engagement and rotation of deployable member 530 with a complimentary screwdriver. While depicted as a hexagonal depression intended to receive an Allen's wrench, any alternative means and arrangements for engaging and rotating the deployable member 530 can be employed including. Likewise, the engageable surface may be placed on the outer surface of head 534 or extend from it.

Adjacent to distal end 516 of elongated body 510, spines are placed which are adaptable to compliment and engage with spines 270 and 1176 of end coupler 270 and 1170 respectively. The spines may be placed on any surfaces of the distal portion 516 of the elongated body 510 or both. Threads 532 of deployable member 530 are engageable to threads 1174 of end coupler 1170 or threads 274 of end coupler 270, thus firmly affixing the modified distraction screw to the plate. The modified distraction screw and the modular distraction screw previously affixed to the adjacent vertebra are used to distract the vertebral bodies, permitting work on the intervening disc space. When the discectomy and subsequent bone work are finished, the modular distraction screw is separated leaving the distal segment attached to vertebral body. The modified distraction screw is removed leaving a bare end-coupler. A separate plate is used to span the distance between the distal segment and the end coupler. In this way, the fusion is readily extended to an adjacent level.

Figure 11B:
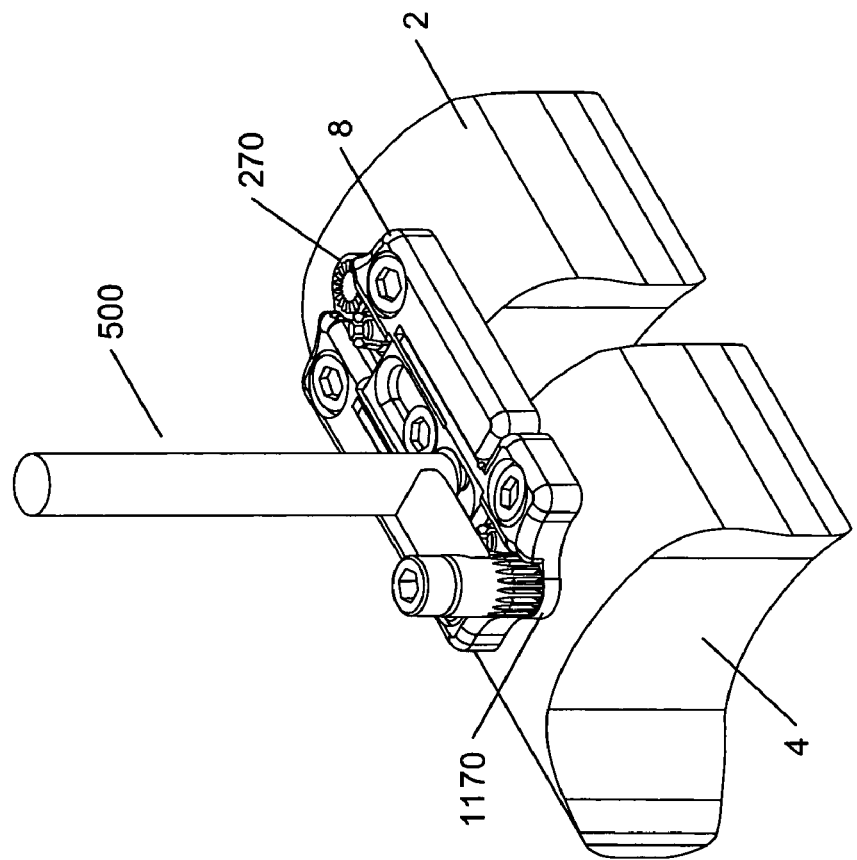
FIG. 11B is a perspective view of an offset, modified distraction screw attached to a bone plate according to an embodiment of the invention.
Figure 11A:
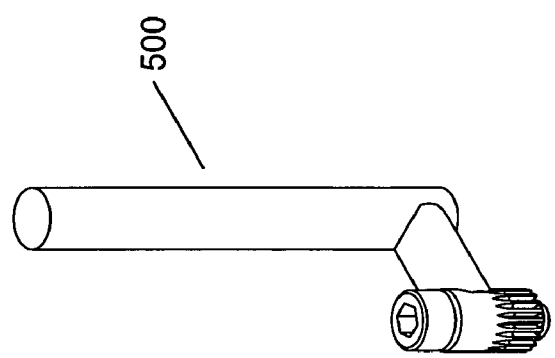
FIG. 11A is a perspective view of an offset, modified distraction screw according to an embodiment of the invention.
Figure 12A:
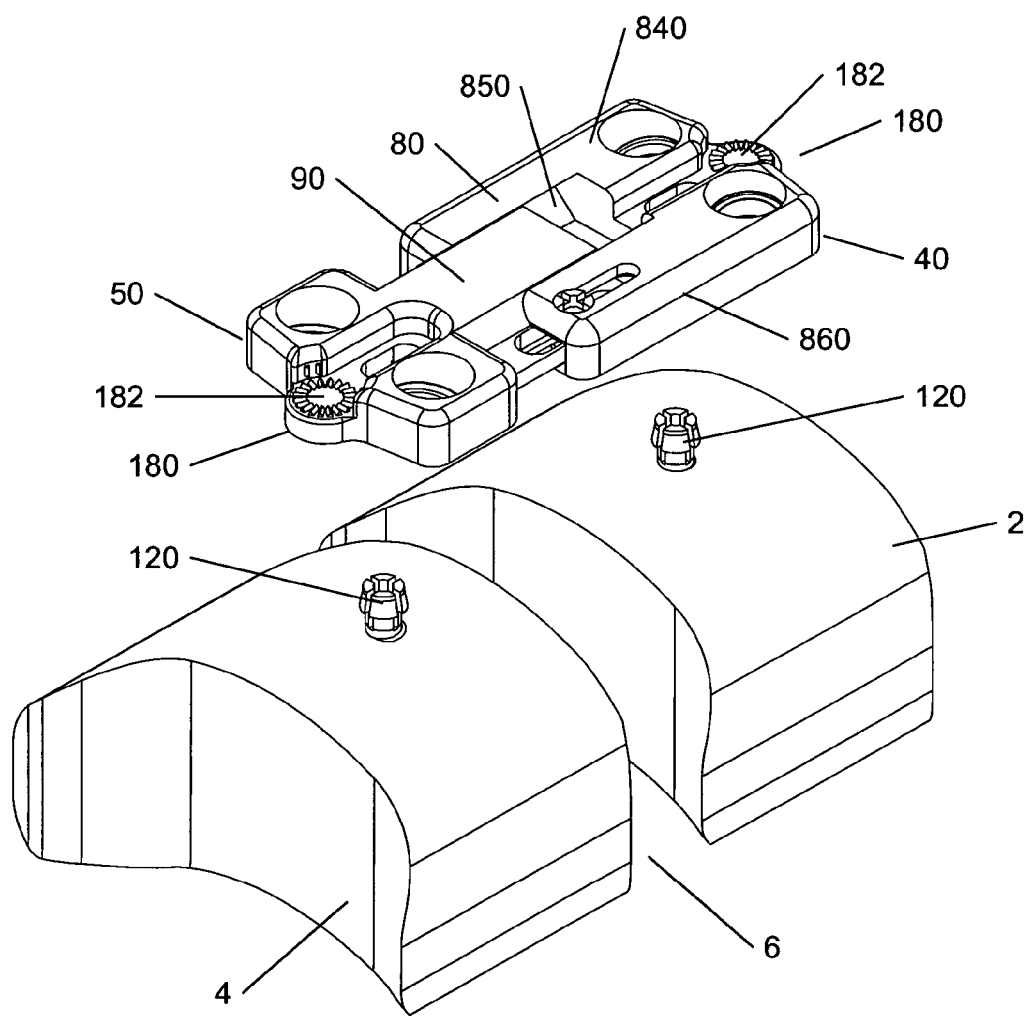
FIG. 12A is an exploded perspective view of a bone plate according to an embodiment of the invention.
Figure 12C:
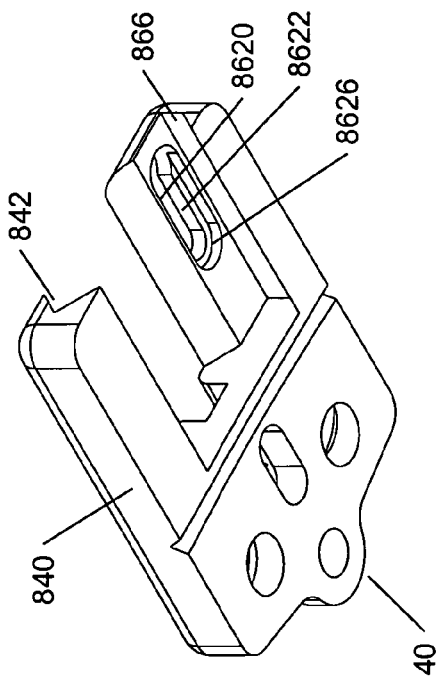
FIG. 12C is a bottom view of a first bone plate component according to an embodiment of the invention.
Figure 12B:
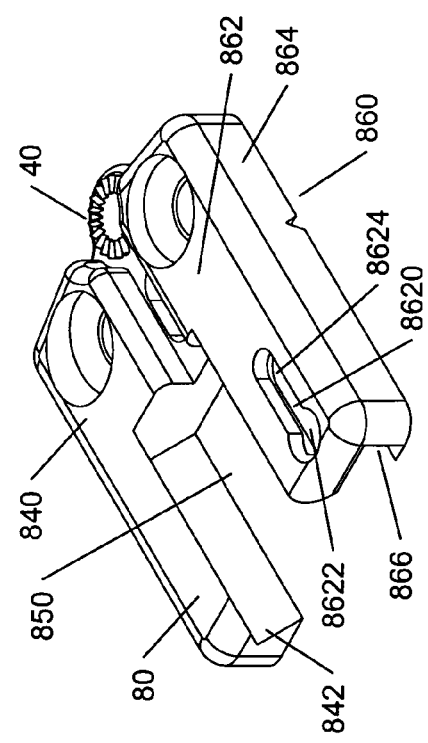
FIG. 12B is a top view of a first bone plate component according to an embodiment of the invention.
Figure 12E:
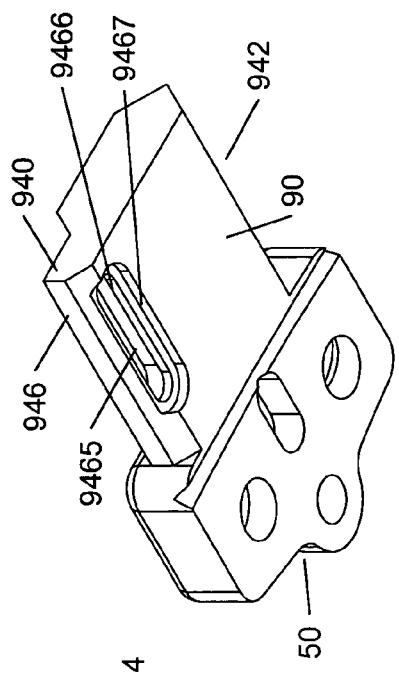
FIG. 12E is a bottom view of a second bone plate component according to an embodiment of the invention.
Figure 12D:
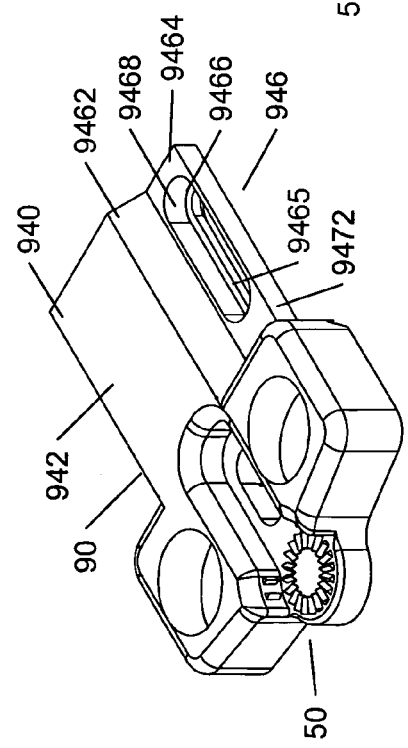
FIG. 12D is a top view of a second bone plate component according to an embodiment of the invention.

Occasionally, placement of the plating segments might result in the end coupler being too close to the adjacent disc space such that placement of the modified distraction screw onto the coupler could hinder surgical access to the disc space. FIG. 11A shows an offset modified distraction screw which may be used in this setting and FIG. 11B illustrates its placement. The screw components are similar to those described above and as shown in FIG. 10.

A further embodiment of the present invention is illustrated in FIGS. 12-16. As in the embodiments described above, the plating segments may be curved in either the vertical or horizontal plane, may contain one or more horizontal indentations in order to permit the placement of additional curvature in the vertical plane (not shown), and may be made of any biologically adaptable or compatible materials.

Each of the plate segments 140 and 150 possess two boreholes to accommodate bone fasteners, a central channel to couple with distal segment 120 of the modular distraction screw and an end-coupler.

A sliding end portion 80 of plate segment 140 is formed by two side projections 840, 860 and a central opening 850. Projection 840 is an extension of the plate segment 80 with side indentation 842. Indentation 842 may be made of any geometric configurations including, but not limited, square, oval, circular, and hybrid designs which is complimentary to wall 942 of projection 940 of plate segment 150. Projection 860 has a top wall 862, a side wall 864 and an inferior wall 866. Preferably, both top and side walls are straight while the inferior wall is triangular. One of ordinary skill in the art would recognize that any geometric configurations may be used for the walls of projection 860 as long as they compliment the interacting surface of slide portion 90 of plate segment 50. Top surface of wall 862 has opening 8620 which is key-hole shaped and composed of a larger, full thickness circular opening 8622 at one end and a partial thickness, slot 8624. The inferior surface of wall 862 has a partial thickness channel with opening 8622 at one end and a channel 8626. The latter is set beneath slot 8624, is of the same length as slot 8624 and of the same width as the diameter of opening 8622.

As shown in FIG. 12, the sliding end portion 90 of plate segment 50 is adapted to fit snuggly within central opening 850 and slidingly engages the inner walls of projections 840 and 860 of plate segment 140. The sliding end portion 90 is formed by projection 940 which has side walls 942 and 946. Wall 942 is depicted as projecting in a ">" fashion but any geometric configuration may be used that compliments surface 842 of plate segment 80. Likewise, wall 946 is configured to compliment 860 of plate segment 80. Preferably, wall 946 has sloping surface 9462 and the partial thickness projection 9464 which has upper wall 9470 and lateral wall 9472. The inferior aspect of wall 9472 is preferably slopped. Partial thickness projection 9464 has channel 9465 and a cross-sectional exploded view is shown in FIG. 13B. The width of channel 9465 is preferably equal to the diameter of opening 8622 of the plate segment 140. A central ridge 9466 is formed along the walls of channel 9465 which is preferably rectangular. Ridge 9466 does not extent to the bottom of channel 9465, leaving channel 9467 beneath the ridge. Preferably, ridge 9466 does not extent to the top of channel 9465, leaving another second channel 9468 above the ridge. The width of the opening formed at the level of ridge 9466 is less than the width of opening 8622.

Plate segments 140 and 150 are coupled in assembly with channel 9465 and opening 8620 overlapping each other by a suitable coupler means. Coupler means incorporates a bolt element 96, which comprises a screw 960 and locking nut 980. Screw 960 has head 962 which is preferably square or hex shaped and fits snuggly beneath ridge 9466 and within channel 9465. The thickness of head 962 is sufficiently thin so as not to extent beyond the inferior surface of projection 9464. Shank 964 of screw 960 is circular and fits within the channel formed at the level of ridge 9466. The shank has a flat end and total length greater than the thickness of projection 9464 but less than the combined thickness of projection 9464 and channel 8626. Shank 964 also has threads 966 (not depicted) which engages nut 980. Nut 980 has a central full thickness bore 982 with threads 984 (not depicted) adapted to compliment and engage threads 966. The threads may be of any available and recognized thread design. Nut 980 fits snuggly within opening 8622 of segment 140, but has diameter greater than that of channel 8624. Preferably, the top surface of nut 980 has indentations 986 which can be engaged by the driving tool.

Figure 14A:
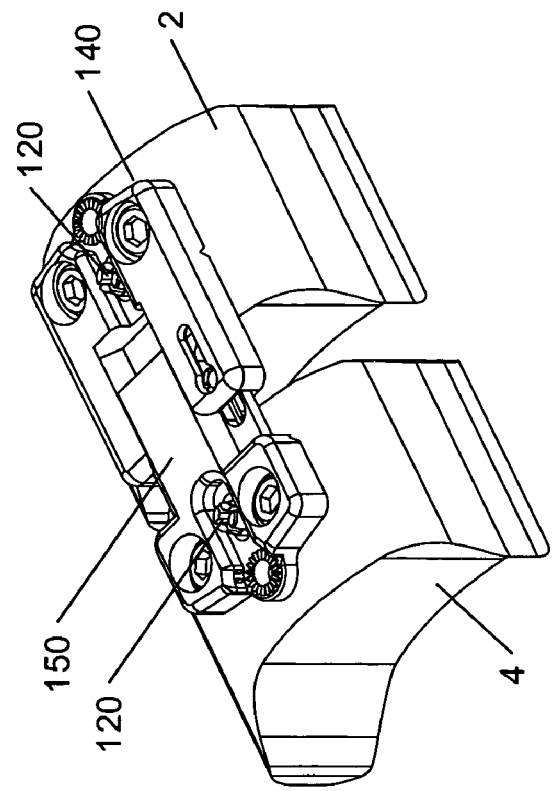
FIG. 14A is a perspective view of a mounted bone plate in an open position according to an embodiment of the invention.
Figure 14B:
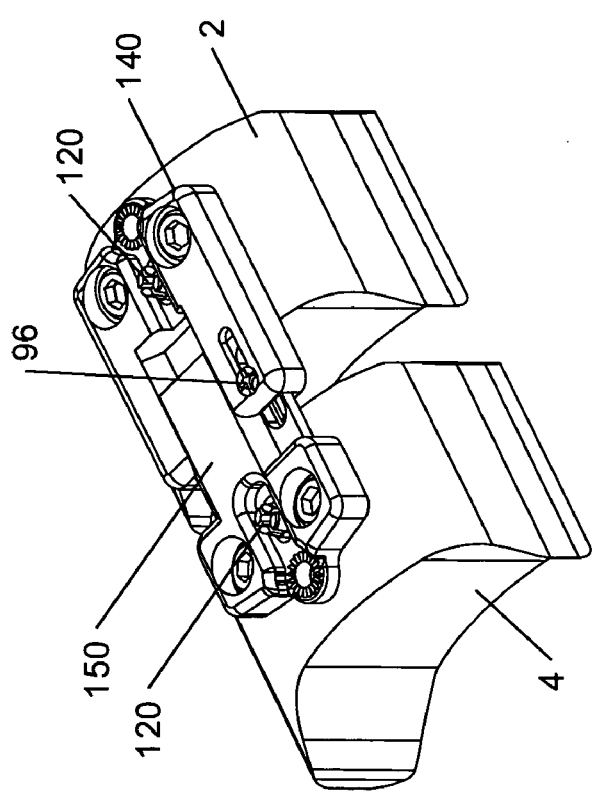
FIG. 14B is a perspective view of a mounted bone plate in a closed position according to an embodiment of the invention.
Figure 15A:
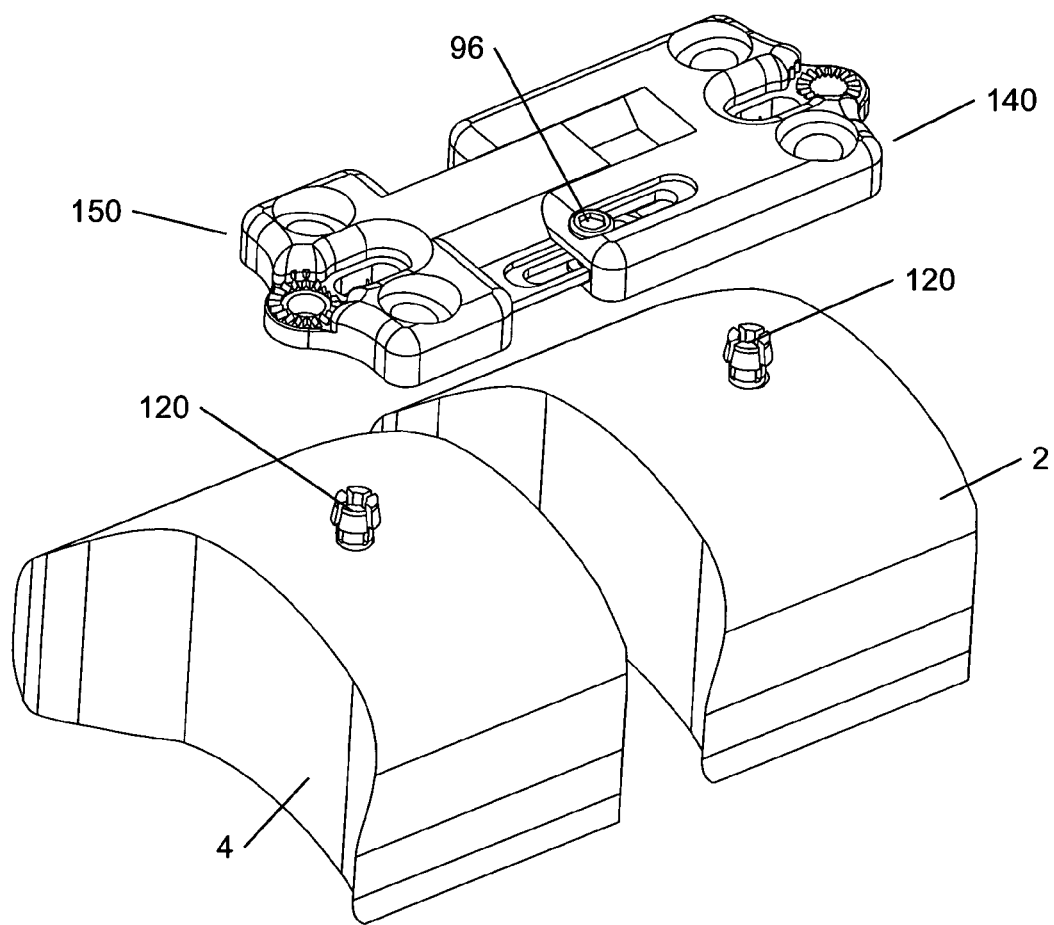
FIG. 15A is an exploded perspective view of a jackscrew bone plate according to an embodiment of the invention.
Figure 15C:
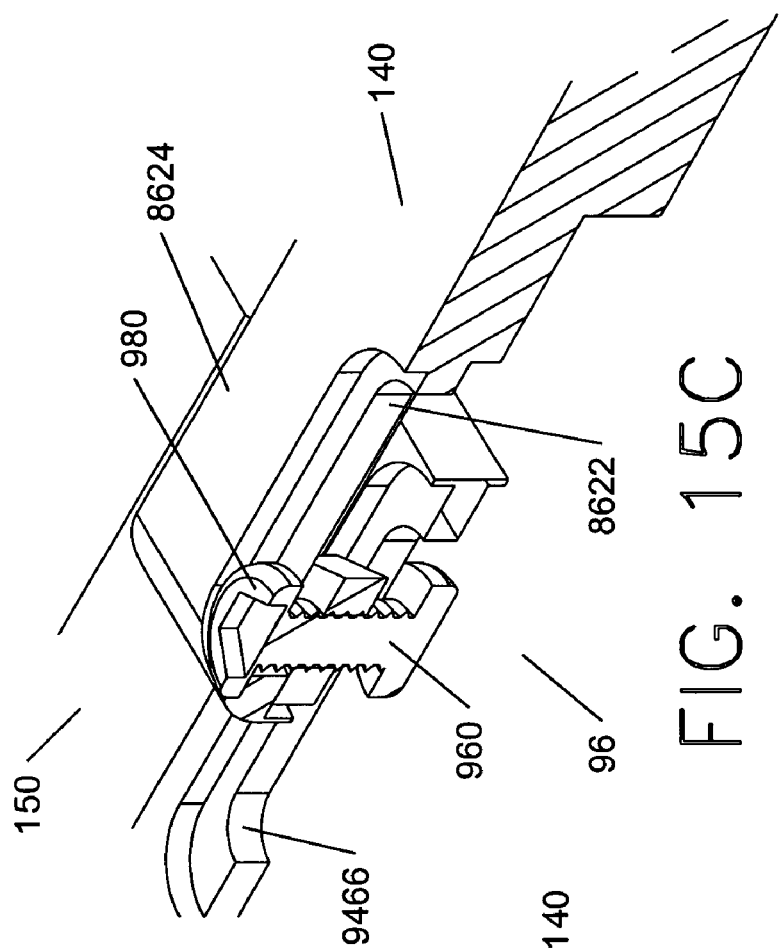
FIG. 15C is a close up sectional view of the locking mechanism of a jack screw bone plate according to an embodiment of the invention.
Figure 15B:
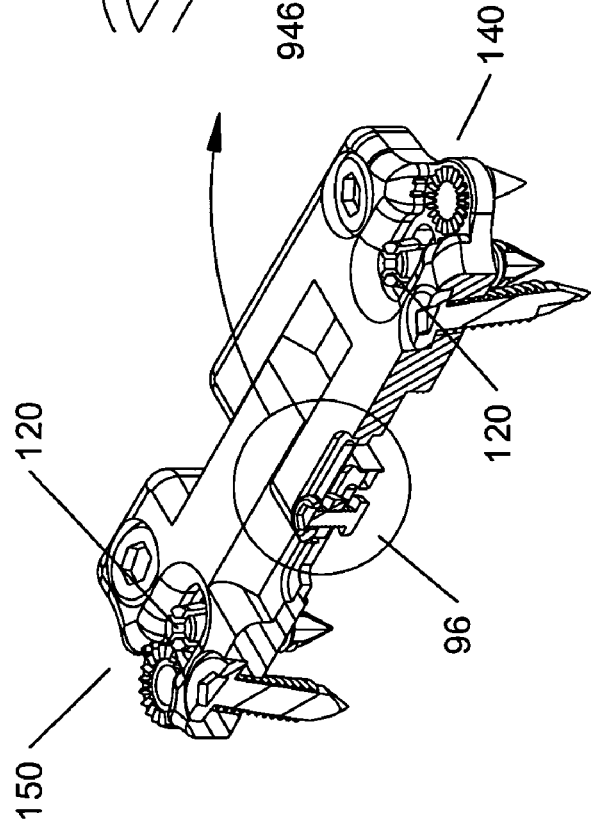
FIG. 15B is a sectional view of a jack screw bone plate according to an embodiment of the invention.
Figure 16A:
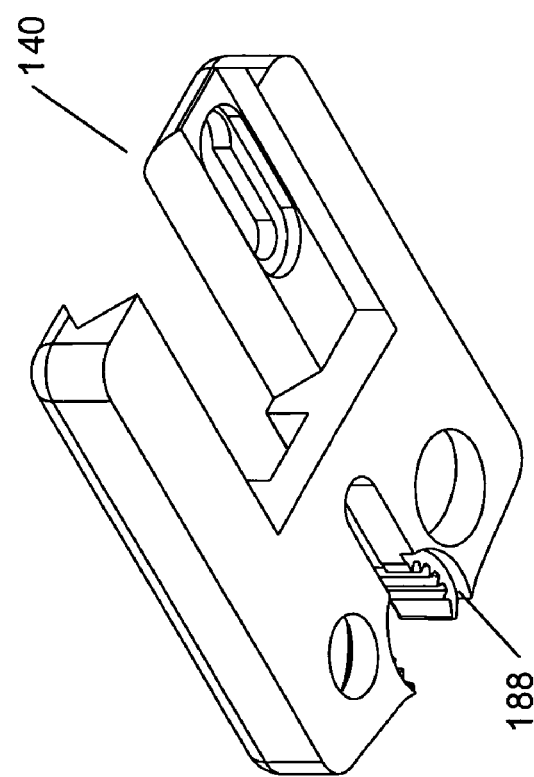
FIGS. 16A-16B are top and bottom views of a bone plate component with an open central channel and an alternative end coupler for a modified distraction screw according to an embodiment of the invention.
Figure 16B:
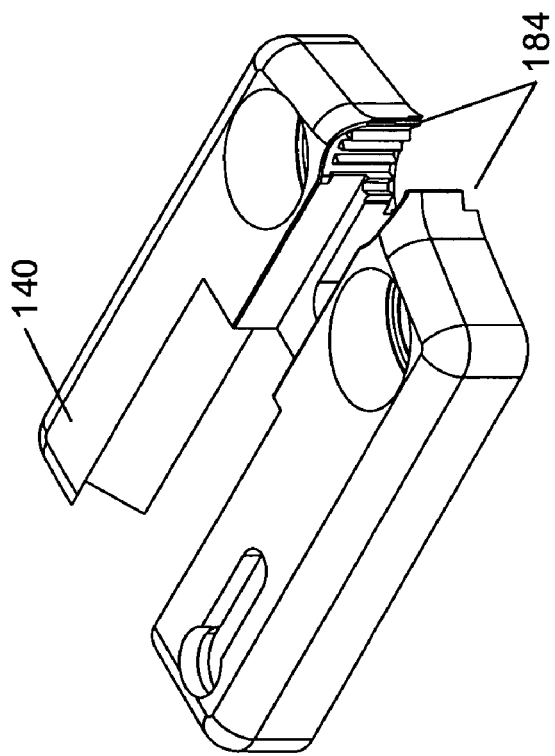

FIGS. 14A and 14B illustrate the coupler means in the open and closed positions. When open, nut 980 of bolt element 96 is held within opening 8622 such that it cannot move relative to plate segment 140. However, since the bolt element 96 is not fixed to plate segment 150, the plate segments 140 and 150 can continue to move relative to one another in either direction. When the plate is set to the desired length, nut 980 is rotated until edge 9466 rests tightly between nut 980 and head 962. The nut 980 also leaves opening 8622 and coming to rest within channel 8626. In this way, bolt element 96 is fixed to plate segment 150 and freed from plate segment 140. If desired, compression may be applied across the fused disc space prior to locking nut 980. Since bolt element 96 rests at the far end of opening 8620, any applied compressive force is maintained with closure of the locking mechanism. After closure, plate segments 140 and 150 can only move towards each other, thus accommodating subsidence. The length of opening 8620 determines the amount of subsidence permitted.

As shown in the drawings, each of the plate segments of the present invention have two boreholes to accommodate bone fasteners, a central channel to couple with distal segment 120 of the modular distraction screw and an end-coupler. These features have been described above and will not be illustrated further.

The plating system of the present invention can be applied, by way of a multilevel plating configuration to fixate three or more bones after the removal of two or more discs. As in the embodiments previously illustrated for single level plate, "multilevel" plates may be curved in either the vertical or horizontal plane, may contain one or more horizontal indentations in order to permit the placement of additional curvature in the vertical plane, and may be made of any biologically adaptable or compatible materials. Each of the upper and lower ends of the plates will contain two boreholes to accommodate bone fasteners, a central slot to anchor the distal segment 120 of the modular distraction screw and an end-coupler to accommodate possible modular extension of the fusion at a later date.

FIG. 17 shows an exemplary embodiment of the multi-level plates, where one of the number of sliding mechanisms can be used at each level such that the total number of sliding mechanisms is equal to the number of discs removed and fused. Longer plates can be made by the sequential addition of other levels. While the illustrated plate present only one exemplary embodiment of the sliding mechanism and coupler means, it is understood that any of the previously discussed embodiments may be used in any combination to produce these plates. Further, different sliding mechanism designs can be used at different levels, if desired.

With the exception of the two ends, a segment 300 with two full thickness bore holes is placed between each of the sliding portions. These boreholes may be oriented in the true vertical plane or form an angle with the vertical. The boreholes will be angled towards each other in the plate's short axis (horizontal plane) and form a right angle with the body of the plate in the long axis (vertical plane). The top opening of the boreholes may be flush with the plate surface or may be recessed. The distance between the boreholes may also vary depending on the requirement of plate application and design.

Removal of two or more discs is accomplished by the step-wise removal of individual discs until all pathological levels have been addressed. Modular distraction screws may be used at each vertebral level if desired, but their use is required only at the upper and lower-most vertebras while conventional distraction screws can be used at all intervening levels. After completion of the bone work, the proximal segments of the distraction screws are removed leaving the distal segments attached to the upper and lower-most vertebral bodies. At other disc levels, the distraction screw can be completely removed after the completion of the bone work.

The plate is guided to proper position along the upper-most and lower-most vertebra by the attached distal segments—as described above for single level procedures. The distal segments of the distraction screws are tightened onto the plate after selection of optimal bone screw position. In this way, the plate is held stationary while the bone screws are placed into the upper and lower-most vertebras and the plate is fixed at each end. Depending on surgeon preference, fixation of the intervening vertebral levels may be started from either end of the plate. For illustration, fixation will be started inferiorly. The plate segment intended to fixate the vertebra immediately superior to the lower-most vertebra is moved into a desired position. The sliding mechanism between this segment and the plate segment attached to the lower-most vertebra is then locked. Once these segments are immobilized, bone screws are placed into the vertebra immediately superior to the lower-most vertebra. The process is repeated at each of the remaining vertebra. If compression is desired across the construct, it's applied across the upper and lower-most vertebras prior to placement of the bone screws into any of the intervening vertebra. Compression is maintained until all the vertebras have been fixed to the plate. Once all sliding mechanisms have been locked, the compression device may be released and the force will be maintained by the plate.

Figure 17A:
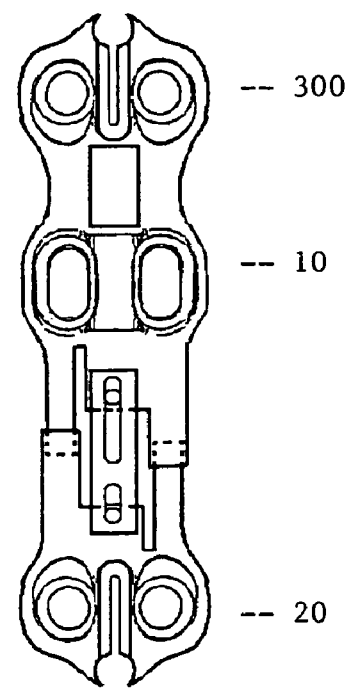
FIGS. 17A-17B are top views of combined bone plates with slotted screw holes and sliding mechanisms according to alternative embodiments of the invention.

Alternatively, one or more sliding mechanisms can be used to accommodate boney subsidence at two or more fused levels. This is accomplished by using a slotted borehole between levels. FIG. 17A illustrates this design feature in a two level plate in which only one sliding mechanism is employed. Again, the plate is placed after completion of the bone work and plate placement is started by fixation of the plate at each end using the distal segments of the distraction screws. The plate is set to the desired length and the sliding mechanism is locked. If desired, compression may be applied prior to closure of the mechanism. The bone screw is placed at the end of the slotted borehole immediately adjacent to the sliding mechanism and the subsidence screw is opened. In this way, the plate's adjustable length and subsidence can be accomplished using a single sliding mechanism. While the second embodiment of the sliding mechanism as well as the alternative embodiments of the end-coupler and central channel are illustrated, it is understood that any of the previously discussed embodiments may be used in any workable combination to produce these plates.

Figure 17B:
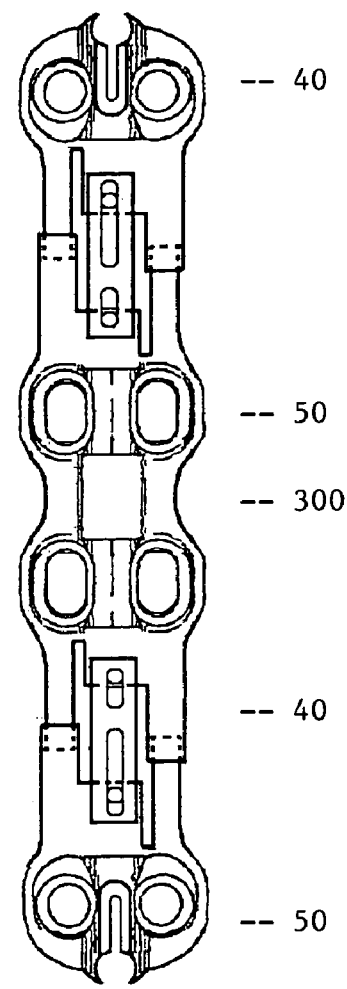

FIG. 17B demonstrates the other potential designs that can be used for a three level plate. Other possible variations that can be used in creating a other multi-level plating system. Longer plates can be made by the sequential addition of other levels.

While the particular systems and methods herein shown and described in detail are fully capable of attaining the above described objects of this invention, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A bone fixation device for retaining at least two bones in a desired spatial relationship, comprising:
   a first member connectable to a first bone;
   a second member connectable to a second bone and interconnected with the first member, wherein the first and second members are movable relative to one another across a range of motion;
   an adjustor member that transitions between a first state wherein the adjustor member is fixed relative to the first member and movable relative to the second member, and a second state wherein the adjustor member is fixed relative to the second member and movable relative to the first member, wherein the range of motion between the first member and second member spans a first, limited distance when the adjustor member is in the first state, and wherein the range of motion between the first member and second member spans a second, limited distance when the adjustor member is in the second state.

2. The device of claim 1, wherein the range of motion enables compression of the bones.

3. The device of claim 1, wherein each of the members has a projection portion and a receiving channel for complemental placement of the projection portion of one member into the receiving channel of another member.

4. The device of claim 1, wherein the first member has at least one projection portion and the second member has at least one receiving channel to receive the projection portion of first member.

5. The device of claim 4, wherein the projection portion has a generally elongated body with cross-section shape selected from the shapes of a triangle, truncated triangle, rectangle, modified rectangle, and a trapezoid.

6. The device of claim 1, wherein the adjustor member comprises an elongated element and a plurality of fasteners for selectively fixing to the first and second members.

7. The device of claim 1, wherein the first and second members each has at least one opening to accommodate a bone screw for securing the first and second members onto the bones.

8. The device of claim 1, wherein at least a portion of the device is constructed of a biologically adaptable or biologically compatible material.

9. The device of claim 1, wherein each of the first and second members has curved surfaces to conform to the surface contours of the bones.

10. A device as in claim 1, wherein the first distance is less than the second distance.

11. A device as in claim 1, wherein the range of motion is linear.

12. A device as in claim 1, wherein the first member includes a distraction screw coupler that permits the first member to be coupled to a distraction screw while the first member is connected to a first bone, wherein the first bone is the first vertebra.

13. A device as in claim 1, wherein the distraction screw coupler comprises a borehole sized to receive therethrough a distraction screw.

14. A device as in claim 13, wherein at least a portion of the borehole can mate with a portion of the distraction screw.

15. A device as in claim 1, wherein the first member includes a modular coupler that can mate with a second bone fixation device.

16. A device as in claim 1, wherein the range of motion is curved.

17. A device as in claim 1, wherein the first and second bones are vertebrae.

18. The device of claim 1, wherein the range of motion enables subsidence of the bones.

* * * * *